United States Patent
Pettus et al.

(10) Patent No.: US 8,420,649 B2
(45) Date of Patent: Apr. 16, 2013

(54) PYRIDO[3,2-D]PYRIDAZINE-2(1H)-ONE COMPOUNDS AS P38 MODULATORS AND METHODS OF USE THEREOF

(75) Inventors: Liping H. Pettus, Thousand Oaks, CA (US); Andrew Tasker, Simi Valley, CA (US); Bin Wu, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/060,675

(22) PCT Filed: Aug. 26, 2009

(86) PCT No.: PCT/US2009/055095
§ 371 (c)(1),
(2), (4) Date: Aug. 1, 2011

(87) PCT Pub. No.: WO2010/025202
PCT Pub. Date: Mar. 4, 2010

(65) Prior Publication Data
US 2011/0281864 A1    Nov. 17, 2011

Related U.S. Application Data

(60) Provisional application No. 61/093,112, filed on Aug. 29, 2008.

(51) Int. Cl.
*A01N 43/58* (2006.01)
*A61K 31/50* (2006.01)

(52) U.S. Cl.
USPC .......................................... 514/250; 544/236

(58) Field of Classification Search .................. 544/236; 514/248, 250
See application file for complete search history.

(56) References Cited

U.S. PATENT DOCUMENTS

| | | | |
|---|---|---|---|
| 5,716,954 | A | 2/1998 | Wilhelm |
| 6,593,325 | B1 | 7/2003 | Carling et al. |
| 6,635,644 | B2 | 10/2003 | Salituro et al. |
| 6,794,380 | B2 | 9/2004 | Brown |
| 2003/0013716 | A1 | 1/2003 | Blackaby et al. |
| 2005/0250782 | A1 | 11/2005 | Marlow |
| 2005/0256123 | A1 | 11/2005 | Marlow et al. |
| 2006/0035897 | A1 | 2/2006 | Caravatti et al. |
| 2006/0199817 | A1 | 9/2006 | Tasker |

FOREIGN PATENT DOCUMENTS

| | | |
|---|---|---|
| WO | 9716442 A1 | 5/1997 |
| WO | 00118001 A1 | 3/2001 |
| WO | 2004010995 A1 | 2/2004 |
| WO | 2005009937 A1 | 2/2005 |
| WO | 2005051301 A1 | 6/2005 |
| WO | 2006094187 A1 | 9/2006 |
| WO | 2007089634 A2 | 8/2007 |

OTHER PUBLICATIONS

Shohami et al., J. Cereb. Blood Flow Metab. 14:615 (1994).
Feurstein et al., Neurosci. Lett. 164:125 (1993).
Feurstein, Stroke 25:1481 (1994).
Clouse et al., J. Immunol. 142:431 (1989).
Landevirta et al., (Am. J. Med. 85:289 (1988).
Abraham, Lancet, 351:929 (1998).
Couriel, Curr. Opinion Oncology, 12:582 (2000).
Labiache, Rheumatology, 43:531 (2004).
Ruan, Cytokine GF Review, 14:447 (2003).
WGET, New England J. Med., 352:351 (2005).
Sugano et al, Mol. Cell Bioch., 266:127 (2004).
Chandrasekhar et al., Clinical Immunol Immunopathol., 55:382 (1990).
Firestein, Am. J. Pathol., 140:1309 (1992).
Dinarello, Eur. Cytokine Netw., 5:517-531 (1994).
Folks et al., J. Immunol., 136:40 (1986).
Beutler et al. (J. Immunol., 135:3969 (1985).
Baracos et al. (New Eng. J. Med., 308:553 (1983).
Brahn et al., Lymphokine Cytokine Res. 11:253 (1992).
Cooper, Clin. Exp. Immunol., 898:244 (1992).
Feldmann et al., Immunological Reviews, pp. 195-223 (1995).
J. Org. Chem. 2005, 70, pp. 5721-5724.
D. E. Trentham et al., J. Exp. Med., 146:857 (1977).
Mitchinson_Ref_-_Substance_Tet_Let_2006.
Haider et al., Communications, 862-864 (1986).
Mitchinson et al., Tetrahedron Letters 47 (2006) 2257-2260.

*Primary Examiner* — Paul V. Ward
(74) *Attorney, Agent, or Firm* — G. Prabhakar Reddy

(57) ABSTRACT

The present invention comprises a new class of compounds useful for the prophylaxis and treatment of protein kinase mediated diseases, including inflammation and related conditions. The compounds have a general Formula I

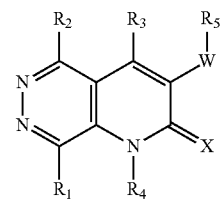

wherein $R^1$, $R^2$, $R^3$, $R^4$, $R^5$, W and X are defined herein. The invention also comprises pharmaceutical compositions including one or more compounds of Formula I, uses of such compounds and compositions for treatment of p38 map kinase mediated diseases including rheumatoid arthritis, psoriasis, chronic obstructive pulmonary disease, pain and other inflammatory disorders, as well as intermediates and processes useful for the preparation of compounds of Formula I.

12 Claims, No Drawings

PYRIDO[3,2-D]PYRIDAZINE-2(1H)-ONE COMPOUNDS AS P38 MODULATORS AND METHODS OF USE THEREOF

RELATED APPLICATIONS

This application is the U.S. national filing, under 35 U.S.C. §371, of International Application No. PCT/US2009/055095, filed Aug. 26, 2009, which application in turn claims the benefit of U.S. Provisional Patent Application No. 61/093,112 filed on Aug. 29, 2008, both specifications of which are hereby incorporated herein by reference in their entireties.

FIELD OF THE INVENTION

The invention relates generally to the field of pharmaceutical agents and, more specifically, to pharmaceutically active compounds, pharmaceutical compositions and methods of use thereof, to treat various disorders, including TNF-α, IL-1β, IL-6 and/or IL-8 mediated diseases and other maladies, such as inflammation and pain. The invention also relates to intermediates and processes useful in the preparation of such compounds.

BACKGROUND OF THE INVENTION

Protein kinases represent a large family of enzymes, which catalyze the phosphorylation of target protein substrates. The phosphorylation is a transfer reaction of a phosphate group from ATP to the protein substrate. Common points of attachment for the phosphate group to the protein substrate include, for example, a tyrosine, serine or threonine residue. Protein tyrosine kinases (PTKs) are enzymes, which catalyze the phosphorylation of specific tyrosine residues in cellular proteins. Examples of kinases in the protein kinase family include, without limitation, abl, Akt, bcr-abl, Blk, Brk, Btk, c-kit, c-Met, c-src, c-fms, CDK1, CDK2, CDK3, CDK4, CDK5, CDK6, CDK7, CDK8, CDK9, CDK10, cRafl, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Due to their activity in numerous cellular processes, protein kinases have emerged as important therapeutic targets.

Protein kinases play a central role in the regulation and maintenance of a wide variety of cellular processes and cellular function. For example, kinase activity acts as molecular switches regulating inflammatory cytokine production via various pathways. Uncontrolled or excessive cytokine production has been observed in many disease states, and particularly in those related to inflammation.

The p38 protein kinase has been reported to be involved in the regulation of inflammatory cytokines. Interleukin-1 (IL-1) and Tumor Necrosis Factor α (also referred to herein as TNF-α or TNF) are pro-inflammatory cytokines secreted by a variety of cells, including monocytes and macrophages, in response to many inflammatory stimuli (e.g., lipopolysaccharide (LPS)) or external cellular stress (e.g., osmotic shock and peroxide).

Elevated levels of TNF-α over basal levels have been implicated in mediating or exacerbating a number of disease states including rheumatoid arthritis (RA); osteoarthritis; rheumatoid spondylitis; gouty arthritis; inflammatory bowel disease (IBD); adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type II diabetes; bone resorption diseases; graft vs. host reaction; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

TNF-α has been reported to play a role in head trauma, stroke, and ischemia. For instance, in animal models of head trauma (rat), TNF-α levels increased in the contused hemisphere (Shohami et al., J. Cereb. Blood Flow Metab. 14:615 (1994)). In a rat model of ischemia wherein the middle cerebral artery was occluded, the levels of TNF-α mRNA of TNF-α increased (Feurstein et al., Neurosci. Lett., 164:125 (1993)). Administration of TNF-α into the rat cortex has been reported to result in significant neutrophil accumulation in capillaries and adherence in small blood vessels. TNF-α promotes the infiltration of other cytokines (IL-1β, IL-6) and also chemokines, which promote neutrophil infiltration into the infarct area (Feurstein, Stroke 25:1481 (1994)).

TNF-α appears to play a role in promoting certain viral life cycles and disease states associated therewith. For instance, TNF-α secreted by monocytes induced elevated levels of HIV expression in a chronically infected T cell clone (Clouse et al., J. Immunol. 142:431 (1989)). Landevirta et al., (Am. J. Med. 85:289 (1988)) discussed the role of TNF-α in the HIV associated states of cachexia and muscle degradation.

TNF-α is upstream in the cytokine cascade of inflammation. As a result, elevated levels of TNF-α may lead to elevated levels of other inflammatory and proinflammatory cytokines, such as IL-1, IL-6, and IL-8. Elevated levels of IL-1 over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; ulcerative colitis; anaphylaxis; muscle degeneration; cachexia; Reiter's syndrome; type II diabetes; bone resorption diseases; ischemia reperfusion injury; atherosclerosis; brain trauma; multiple sclerosis; sepsis; septic shock; and toxic shock syndrome. Viruses sensitive to TNF-α inhibition, e.g., HIV-1, HIV-2, HIV-3, are also affected by IL-1.

Antagonism of TNF-α has been reported to be beneficial for treating uveitis (Reiff et al, A&R 44:141-145 (2001)); Sepsis (Abraham, Lancet, 351:929 (1998)); Systemic Lupus Erythrematosis (SLE) (Aringer, A&R, 50:3161 (2004)); Graft vs Host Disease (Couriel, Curr. Opinion Oncology, 12:582 (2000)); Polymyositis and Dermatomyositis (Labiache, Rheumatology, 43:531 (2004)); Type II diabetes (Ruan, Cytokine GF Review, 14:447 (2003)); Sjogren's disease (Marriette, A&R, 50:1270 (2004)), Sarcoidosis (Roberts, Chest, 124:2028 (2003)); Wegener's granulomatosis (WGET, New England J. Med., 352:351 (2005)) and post MI cardiac dysfunction (Sugano et al, Mol. Cell. Bioch., 266:127 (2004)). In addition, TNF-α has been reported to play a role in SAPHO, periodic fever, relapsing polychrondritis, multicentric reticulohistiocytosis, macrophage activation syndrome, Hyper IgD syndrome, familial Hibernian fever, Pyoderma gangrenosum, Cochleovestibular disorders, Cicatrical pemphigoid, Herniated intervertebral disc diseases, amyloidosis, CINCA syndrome, myelodisplastic syndrome, alcoholic hepatitis, and endometriosis. Finally, indications which have already been approved for treatment with a therapeutic agent which modulates TNF-α levels in the plasma, and/or other pro-inflammatory cytokines, include without limitation, inflammatory bowel disease (IBD), psoriatis arthritis, ankylosing spondylitis and juvenile RA.

TNF-α and IL-1 appear to play a role in pancreatic β cell destruction and diabetes. Pancreatic β cells produce insulin which helps mediate blood glucose homeostasis. Deterioration of pancreatic β cells often accompanies type I diabetes. Pancreatic β cell functional abnormalities may occur in patients with type II diabetes. Type II diabetes is characterized by a functional resistance to insulin. Further, type II diabetes is also often accompanied by elevated levels of plasma glucagon and increased rates of hepatic glucose production. Glucagon is a regulatory hormone that attenuates liver gluconeogenesis inhibition by insulin. Glucagon receptors have been found in the liver, kidney and adipose tissue. Thus, glucagon antagonists are useful for attenuating plasma glucose levels (WO 97/16442, incorporated herein by reference in its entirety). By antagonizing the glucagon receptors, it is thought that insulin responsiveness in the liver will improve, thereby decreasing gluconeogenesis and lowering the rate of hepatic glucose production. Elevation of glucose levels along with the reduced expression of IL-1Ra, an antagonist of IL-1 signaling, leads to impaired insulin secretion, decreased cell proliferation and apoptosis. Inhibition of IL-1 action has been shown to improve glycemia, b-cell secretory function and reduce markers of systemic inflammation (Larsen, New England J. Med., 356: 1517 (2007).

In rheumatoid arthritis models in animals, multiple intra-articular injections of IL-1 led to an acute and destructive form of arthritis (Chandrasekhar et al., Clinical Immunol Immunopathol., 55:382 (1990)). In studies using cultured rheumatoid synovial cells, IL-1 is a more potent inducer of stromelysin than is TNF-α (Firestein, Am. J. Pathol., 140: 1309 (1992)). At sites of local injection, neutrophil, lymphocyte, and monocyte emigration has been observed. The emigration is attributed to the induction of chemokines (e.g., IL-8), and the up-regulation of adhesion molecules (Dinarello, Eur. Cytokine Netw., 5:517-531 (1994)).

IL-1 also appears to play a role in promoting certain viral life cycles. For example, cytokine-induced increase of HIV expression in a chronically infected macrophage line has been associated with a concomitant and selective increase in IL-1 production (Folks et al., J. Immunol., 136:40 (1986)). Beutler et al. (J. Immunol., 135:3969 (1985)) discussed the role of IL-1 in cachexia. Baracos et al. (New Eng. J. Med., 308:553 (1983)) discussed the role of IL-1 in muscle degeneration.

In rheumatoid arthritis (RA), both IL-1 and TNF-α induce synoviocytes and chondrocytes to produce collagenase and neutral proteases, which leads to tissue destruction within the arthritic joints. In an in-vivo animal model of arthritis, i.e., collagen-induced arthritis (CIA) in rats and mice, intra-articular administration of TNF-α either prior to or after the induction of CIA led to an accelerated onset of arthritis and a more severe course of the disease (Brahn et al., Lymphokine Cytokine Res. 11:253 (1992); and Cooper, Clin. Exp. Immunol., 898:244 (1992)). IL-1 and TNF-α have been implicated in pro-inflammatory mechanisms in many human diseases including inflammatory arthritis, inflammatory bowel disease sepsis syndrome and both acute and cheonis inflammation of many organs. (Vassali P., The Pathophysiology of Tumor Necrosis Factors, Ann. Rev. Immunology 10: 411-452 (1992) and Dinarello C A, Biologic Basis for Interluekin-1 in disease, Blood, 87:2095-2147 (1996)).

IL-6 also appears to play a role in, and therefore have applications to, pro-inflammatory and other malignant diseases. Particularly, deregulated levels of IL-6 are associated with various immunological diseases, such as RA, systemic juvenile idiopathic arthritis (sJIA), polyarticular type JIA, systemic lupus erythematosus (SLE), vasculitis syndrome, Castleman Disease and Crohn's Disease; transplantation conditions such as acute rejection and graft-versus-host disease (GVHD); respiratory diseases such as interstitial pneumonia and bronchial; asthma; bone diseases such as osteoporosis and Paget's disease, as well as various malignant disease including multiple myeloma, renal cancer, prostate cancer, cardiac mixoma, Kaposis sarcoma, Mesothelioma, Malignant lymphoma, lung cancer and gastric cancer. (Nishimoto and Kishimoto, Review, 2: 619-625 (2006)). It follows that the reduction and/or regulation of IL-6 levels may be useful for treatment of one or more of the above diseases.

IL-8 has been implicated in exacerbating and/or causing many disease states in which massive neutrophil infiltration into sites of inflammation or injury (e.g., ischemia) is mediated by the chemotactic nature of IL-8, including, but not limited to, the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 also has the ability to activate neutrophils. Thus, reduction in IL-8 levels may lead to diminished neutrophil infiltration.

The role and activity of the p38 protein in RA and other pro-inflammatory cytokine mediated diseases and conditions are becoming better understood. For example, Korb et al., Arthritis and Rheumatism, 54: 2745-2756 (2006) describes the activation of the p38 alpha (p38α) and p38 gamma (p38γ) and the role which these two isoforms play in the development and progression of RA. Korb further describes the correlation between expression of p38 and the incidence of CRP in RA. Korb has found that the expression of these isoforms dominate in patients with chronic inflammation and, therefore, concludes that effective strategies to inhibit p38 kinase should aim to specifically target either or both of the isoforms. Medicherla et al., J. Pharmacology and Experimental Therapeutics, 318, 132-141 (2006) and Nishikawa et al., Arthritis & Rheumatism, 48, 2670-2681 (2003) describe results of an in-vivo collegan-induced arthritis (CIA) model in the rat and mouse. More specifically, they report that, in both animals, inhibition of p38α activity and related signaling improved clinical score and reversed bone and cartilage destruction. Ferrari, Cardiovascular Research 37:554 (1998) and Jacobsson et al., J Rheum. 32:1213 (2005) describe how pro-inflammatory cytokines, such as TNF and IL-1, play a role in cadiovascular disease. More specifically, they have found that blocking or reducing the levels of TNF-α have a protective effect, and reduce the incidence of cardiovascular disease in RA patients. Behr et al., Circulation, 104, 1292 (2001) describes the ability and efficacy of a p38 kinase inhibitor in treating hypertensive cardiac hypertrophy.

Proof of biological connection between the role and function of p38α map kinase pro-inflammatory cytokine production is very clear. Though p38α null mice are not viable, embryonic stem cells taken from these mice show a reduced capacity for IL-1 induced production and activation of MAP kinase-activated protein kinase-2 (MAPKAP-2), a downstream substrate of p38α map kinase in response to stress (*J. Exp. Med.* 191, 859-869, 2000). More importantly, MAPKAP-2 deficient mice also show diminished production of IL-6 and TNF ((Kotlyarov, A. et al, "MAPKAP kinase 2 is Essential for LPS-induced TNF-α Biosynthesis", *Nature Cell Biology,* 1, 94-97, 1999). So p38α/MAPKAP pathway is crucial to inflammatory cytokine production and signaling. Furthermore, p38α phosphorylates a variety of transcriptional factors, some of which are responsible for transcription expression of genes encoding inflammatory cytokines (Kumar, S. et al, "p38 MAP kinases: key signaling molecules as Therapeutic targets for Inflammatory Disease", *Nature Review Drug Discovery*, 2, 717-726, 2003).

Rheumatoid arthritis (RA) is a common inflammatory disease of synovial joints and is characterized by the production of pro-inflammatory cytokines/mediators by immune cells that infiltrate synovium. This causes proliferation of synovial fibroblasts, further release cytokine inflammatory molecules and formation of pannus tissue that eventually degrades cartilage and subchondral bone, leading to joint destruction, pain and disability. IL-1 and TNF are the two most important inflammatory cytokines in stimulating the destructive cascade of inflammation pathway, the production of secondary mediators, such as prostaglandins E2 (PGE2) matrix metalloproteinases and vascular cell adhesion molecules and others. Agents that restrict the availability of TNF or IL-1 have been sho9wn to be efficacious in animal models and in the clinic for RA and Crohn's Disease.

There have been commercial successes targeting reduction of TNF. The anti-TNF antibody infliximab (Remicade, Centicore) and the TNF receptor-Fc fusion protein Etanercept (Enbrel; Amgen) bind to TNF and prevent it from binding to cell surface receptors, thereby inhibiting its biological actions Anakinra (Kineret; Amgen), a soluble IL-1 receptor antagonist has been approved for the treatment of RA by the US regulatory authority (Food and Drug Administration or FDA). Enbrel has been approved by the US FDA for moderate to severe RA, juvenile RA, ankylosing spondylitis, plaque psoriasis, and psoriatic arthritis. Adalimumab (Humira), which binds to TNFα and prevents activation of the TNF receptor, has also been approved for commercial use for similar indications.

In addition, there are a number of small molecule p38 inhibitors which have been approved by the FDA, based on safety and efficacy data in animal models, for clinical trials in humans. These agents are undergoing safety and therapeutic efficacy trials, notably for RA, but also for other TNF related conditions, including, without limitation, Crohn's, MS, psoriasis, related dermatitis, and other indications which have been approved or are clearly connected with pro-inflammatory cytokines such as TNF and IL-1. Other TNF related indications are arising as well. For instance, Array 797, a small molecule p38 inhibitor, is in phase II trials for treating pain in dental patients.

Consequently, many approaches to treating pro-cytokine mediated inflammatory diseases and conditions have been conducted. For example, small molecule SB-203580a traryl imidazole, was developed as a pharmacological tool to show a correlation between the binding of the compound inside the cell to inhibit the natural function of p38α and the inhibition of cell cytokine synthesis (*Nature* 372, 739-746, 1994).

Several approaches have been taken to block the effect of TNF-α. One approach involves using soluble receptors for TNF-α (e.g., TNFR-55 or TNFR-75), which have demonstrated efficacy in animal models of TNF-α-mediated disease states. A second approach to neutralizing TNF-α using a monoclonal antibody specific to TNF-α, cA2, has demonstrated improvement in swollen joint count in a Phase II human trial of rheumatoid arthritis (Feldmann et al., *Immunological Reviews*, pp. 195-223 (1995)). These approaches block the effects of TNF-α and IL-1 by either protein sequestration or receptor antagonism.

Yet another approach to block the effect of TNF-α, and other pro-inflammatory cytokines, has been to modulate the activity of the p38 kinase enzyme. For example, the PCT publication, WO 04/010995, published on Feb. 5, 2004, describes fused heteroaryl derivatives for use as p38 kinase inhibitors in the treatment of I.A. and rheumatoid arthritis; PCT publication, WO 2005/009937, published on Feb. 3, 2005, describes 5-membered heterocycle-based p38 kinase inhibitors; U.S. Pat. No. 6,635,644, issued Oct. 21, 2003, describes fused nitrogen-containing bicyclic ring systems as p38 inhibitors; and U.S. Pat. No. 6,794,380, issued Sep. 21, 2004, describes amide derivatives as p38 inhibitors. Despite the ongoing efforts, there needs to be effective anti-inflammatory agents which regulate the production of pro-inflammatory cytokines, including TNF-α, IL-1β, IL-6 and/or IL-8, to treat related diseases and conditions.

BRIEF DESCRIPTION OF THE INVENTION

The present invention provides a new class of compounds useful in the prophylaxis and treatment of diseases mediated by pro-inflammatory cytokines, such as TNF-α, IL-1β, IL-6 and/or IL-8. The compounds, including stereoisomers, tautomers, solvates, pharmaceutically acceptable salts, derivatives or prodrugs thereof, are generally defined by Formula I

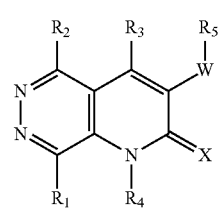

wherein $R^1$, $R^2$, $R^3$, $R^4$, $R^5$, W and X are described below. The invention also provides procedures for making compounds of Formula I, compounds of Formula II, and intermediates useful in such procedures.

The compounds provided by the invention are capable of modulating the p38 kinase protein. To this end, the compounds of the invention are useful for regulating the levels of pro-inflammatory cyclokines and for therapeutic, prophylactic, acute and/or chronic treatment of TNF-α, IL-1β, IL-6 and/or IL-8 mediated diseases, such as those described herein. For example, the compounds are useful for the prophylaxis and treatment of RA, pain, and other conditions involving inflammation. In another embodiment, the invention provides pharmaceutical compositions, also commonly referred to as "medicaments", comprising one or more of the compounds of the invention in combination with one or more pharmaceutically acceptable carrier(s) or excipient(s). Such pharmaceutical compositions are useful to attenuate, alleviate, or treat p38 kinase-mediated disorders through inhibition of the activity of the p38 kinase enzyme.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts, derivatives or prodrugs thereof, are defined by general Formula I:

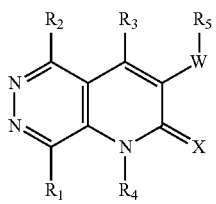

wherein

R¹ is $C_{1-8}$-alkyl, $-OC_{1-8}$-alkyl, $-SC_{1-8}$-alkyl, $-NHC_{1-8}$-alkyl, $-N(C_{1-8}$-alkyl$)_2$, $C_{2-8}$-alkenyl, $C_{2-8}$-alkynyl or $C_{3-8}$-cycloalkyl, each of which is optionally substituted with 1-5 substituents of $R^6$, or R¹ is a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with 1-5 substituents of $R^6$;

each of R² and R³, independently, is H, halo, haloalkyl, $NO_2$, CN, $C_{1-6}$-alkyl, $C_{1-6}$-alkoxyl, $C_{1-6}$-thioalkyl, $C_{1-6}$-aminoalkyl, $C_{2-6}$-alkenyl, $C_{2-6}$-alkynyl or $C_{3-6}$-cycloalkyl, each of the $C_{1-6}$-alkyl, $C_{2-6}$-alkenyl, $C_{2-6}$-alkynyl and $C_{3-10}$-cycloalkyl optionally substituted with 1-5 substituents of $R^6$;

R⁴ is CN, C(O)R⁶, $C_{1-6}$-alkyl, $-OC_{1-6}$-alkyl, $C_{2-6}$-alkenyl, $C_{2-6}$-alkynyl or $C_{3-6}$-cycloalkyl, each of the $C_{1-6}$-alkyl, $-OC_{1-6}$-alkyl, $C_{2-6}$-alkenyl, $C_{2-10}$-alkynyl and $C_{3-6}$-cycloalkyl optionally substituted with 1-5 substituents of $R^6$;

R⁵ is a partially or fully saturated or fully unsaturated 3-6 membered monocyclic, ring of carbon atoms optionally including 1-3 heteroatoms selected from O, N, or S, and optionally substituted independently with 1-5 substituents of $R^6$;

each $R^6$, independently, is F, Cl, Br, I, $CF_3$, $C_2F_5$, CN, OH, $NO_2$, $NH_2$, acetyl, oxo, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}-C_{1-6}$-alkoxyl, $C_{1-6}$-thioalkoxyl, $-SO_2C_{1-6}$-alkyl or a saturated or partially or fully unsaturated 5-6 membered monocyclic ring formed of carbon atoms optionally including 1-3 heteroatoms selected from O, N, or S and optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine or diisopropylamine;

W is O, S, NH or $NCH_3$; and

X is O or S.

In one embodiment, the invention provides compounds of Formula I wherein R¹ is $C_{1-8}$-alkyl, $-OC_{1-8}$alkyl, $-SC_{1-8}$-alkyl, $-NHC_{1-8}$alkyl, $-N(C_{1-8}$-alkyl$)_2$, $C_{2-8}$-alkenyl, $C_{2-8}$-alkynyl or $C_{3-8}$-cycloalkyl, each of which is optionally substituted with 1-5 substituents of $R^6$, in conjunction with any of the above or below embodiments.

In another embodiment, the invention provides compounds of Formula I wherein R¹ is $C_{1-6}$-alkyl, $-OC_{1-6}$-alkyl, $-SC_{1-6}$-alkyl, $-NHC_{1-6}$-alkyl, $-N(C_{1-6}$-alkyl, $C_{2-6}$-alkyl, $C_{2-6}$-alkynyl or $C_{3-6}$-cycloalkyl, each of which is optionally substituted with 1-5 substituents of $R^6$, in conjunction with any of the above or below embodiments.

In another embodiment, the invention provides compounds of Formula I wherein R¹ is methyl, ethyl, propyl, isopropyl, butyl, sec-butyl, tert-butyl, pentyl, neo-pentyl, isopentyl, cyclopropyl, cyclobutyl, cyclopentyl, cyclohexyl, $-OC_{1-4}$-alkyl, $-SC_{1-4}$-alkyl, $NHC_{1-4}$-alkyl or $-N(C_{1-4}$-alkyl$)_2$, each of which is optionally substituted with 1-5 substituents of $R^6$, in conjunction with any of the above or below embodiments.

In another embodiment, the compounds of Formula I includes compounds wherein R¹ is methyl, ethyl, propyl, isopropyl, butyl, isobutyl, sec-butyl, pentyl, neopenyl, hexyl, cyclopropyl, cyclopentyl, cyclohexyl or allyl, each of which is optionally comprising 1-4 heteroatoms selected from N, O and S and optionally substituted with one or more substituents of $R^6$, in conjunction with any of the above or below embodiments.

In another embodiment, the invention provides compounds of Formula I wherein R¹ is a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with 1-5 substituents of $R^6$, in conjunction with any of the above or below embodiments.

In another embodiment, the invention provides compounds of Formula I wherein R¹ is a phenyl, pyridyl, pyrimidyl, triazinyl, pyridazinyl, pyrazinyl, thiophenyl, furyl, tetrahydrofuryl, pyrrolyl, tetrahydropyrrolyl, pyrazolyl, imidazolyl, triazolyl, tetrazolyl, thiazolyl, oxazolyl, oxazolinyl, isoxazolyl, isoxazolinyl, oxadiazolyl, isothiazolyl, morpholinyl, piperidinyl, piperazinyl, pyranyl, cyclopropyl, cyclobutyl, cyclopentyl or cyclohexyl, each of which is optionally substituted independently with 1-5 substituents of $R^6$, in conjunction with any of the above or below embodiments.

In another embodiment, the invention provides compounds of Formula I wherein R¹ is a phenyl, pyridyl, pyrimidyl, triazinyl, pyridazinyl, pyrazinyl, thiophenyl, furyl, tetrahydrofuryl, pyrrolyl, pyrazolyl, imidazolyl, triazolyl, tetrazolyl, thiazolyl, oxazolyl, isoxazolyl, oxadiazolyl, isothiazolyl, morpholinyl, piperidinyl, piperazinyl, each of which is optionally substituted independently with 1-5 substituents of $R^6$, in conjunction with any of the above or below embodiments.

In another embodiment, the invention provides compounds of Formula I wherein R¹ is a phenyl, pyridyl, pyrimidyl, pyridazinyl, pyrazinyl, thiophenyl, furyl, pyrrolyl, pyrazolyl, imidazolyl, morpholinyl, piperidinyl, piperazinyl, each of which is optionally substituted independently with 1-5 substituents of $R^6$, in conjunction with any of the above or below embodiments.

In another embodiment, the invention provides compounds of Formula I wherein R¹ is a phenyl, pyridyl, pyrimidyl, pyridazinyl or pyrazinyl, each of which is optionally substituted independently with 1-5 substituents of $R^6$, in conjunction with any of the above or below embodiments.

In another embodiment, the invention provides compounds of Formula I wherein R¹ is a phenyl optionally substituted independently with 1-5 substituents of $R^6$, in conjunction with any of the above or below embodiments.

In another embodiment, the invention provides compounds of Formula I wherein R¹ is methyl, ethyl, propyl, isopropyl, butyl, sec-butyl, tert-butyl, pentyl, neo-pentyl, isopentyl, cyclopropyl, cyclobutyl, cyclopentyl, cyclohexyl, $-OC_{1-4}$-alkyl, $-SC_{1-4}$-alkyl, $-NHC_{1-4}$-alkyl or $-N(C_{1-4}$-alkyl$)_2$, each of which is optionally substituted with 1-5 substituents of $R^6$, or R¹ is a ring selected from phenyl, pyridyl, pyrimidyl, triazinyl, pyridazinyl, pyrazinyl, thiophenyl, furyl, tetrahydrofuryl, pyrrolyl, pyrazolyl, imidazolyl, triazolyl, tetrazolyl, thiazolyl, oxazolyl, isoxazolyl, oxadiazolyl, isothiazolyl, morpholinyl, piperidinyl, piperazinyl, each ring of which is optionally substituted independently with 1-5 substituents of $R^6$, in conjunction with any of the above or below embodiments.

In another embodiment, the invention provides compounds of Formula I wherein $R^2$ is H, halo, haloalkyl, $NO_2$, CN, $C_{1-6}$-alkoxyl, $C_{1-6}$-thioalkyl, $C_{1-6}$-aminoalkyl, $C_{2-6}$-alkenyl, $C_{2-6}$-alkynyl or $C_{3-6}$-cycloalkyl, each of the $C_{1-6}$-alkyl, $C_{2-6}$-alkenyl, $C_{2-6}$-alkynyl and $C_{3-10}$-cycloalkyl optionally substituted with 1-5 substituents of $R^6$, in conjunction with any of the above or below embodiments.

In another embodiment, the invention provides compounds of Formula I wherein $R^2$ is H, halo, haloalkyl, $NO_2$, CN, $C_{1-6}$-alkyl, $C_{1-6}$-alkoxyl or $C_{1-6}$-aminoalkyl, each of which are optionally substituted with 1-5 substituents of $R^6$, in conjunction with any of the above or below embodiments.

In another embodiment, the invention provides compounds of Formula I wherein $R^2$ is H, halo, haloalkyl or $C_{1-6}$-alkyl, in conjunction with any of the above or below embodiments.

In another embodiment, the invention provides compounds of Formula I wherein $R^2$ is H, halo, methyl or ethyl, in conjunction with any of the above or below embodiments.

In another embodiment, the invention provides compounds of Formula I wherein $R^2$ is H, F, Cl, methyl or ethyl, in conjunction with any of the above or below embodiments.

In another embodiment, the invention provides compounds of Formula I wherein $R^2$ is H, in conjunction with any of the above or below embodiments.

In another embodiment, the invention provides compounds of Formula I wherein $R^3$ is H, halo, haloalkyl, $NO_2$, CN, $C_{1-6}$-alkoxyl, $C_{1-6}$-thioalkyl, $C_{1-6}$-aminoalkyl, $C_{2-6}$-alkenyl, $C_{2-6}$-alkynyl or $C_{3-6}$-cycloalkyl, each of the $C_{1-6}$-alkyl, $C_{2-6}$-alkenyl, $C_{2-6}$-alkynyl and $C_{3-10}$-cycloalkyl optionally substituted with 1-5 substituents of $R^6$, in conjunction with any of the above or below embodiments.

In another embodiment, the invention provides compounds of Formula I wherein $R^3$ is H, halo, haloalkyl, $NO_2$, CN, $C_{1-6}$-alkoxyl or $C_{1-6}$-aminoalkyl, each of which are optionally substituted with 1-5 substituents of $R^6$, in conjunction with any of the above or below embodiments.

In another embodiment, the invention provides compounds of Formula I wherein $R^3$ is H, halo, haloalkyl or $C_{1-6}$-alkyl, in conjunction with any of the above or below embodiments.

In another embodiment, the invention provides compounds of Formula I wherein $R^3$ is H, halo, methyl or ethyl, in conjunction with any of the above or below embodiments.

In another embodiment, the invention provides compounds of Formula I wherein $R^3$ is H, F, Cl, methyl or ethyl, in conjunction with any of the above or below embodiments.

In another embodiment, the invention provides compounds of Formula I wherein $R^3$ is H, in conjunction with any of the above or below embodiments.

In another embodiment, the invention provides compounds of Formula I wherein each of $R^2$ and $R^3$, independently, is H or halo, in conjunction with any of the above or below embodiments.

In another embodiment, the invention provides compounds of Formula I wherein each of $R^2$ and $R^3$, independently, is H, F, Cl, methyl or ethyl, in conjunction with any of the above or below embodiments.

In another embodiment, the invention provides compounds of Formula I wherein each of $R^2$ and $R^3$, independently, is H or F, in conjunction with any of the above or below embodiments.

In another embodiment, the invention provides compounds of Formula I wherein each of $R^2$ and $R^3$, independently, is H, in conjunction with any of the above or below embodiments.

In another embodiment, the invention provides compounds of Formula I wherein $R^4$ is CN, $C(O)R^9$, $C_{1-6}$-alkyl, $-OC_{1-6}$-alkyl, $C_{2-6}$-alkenyl, $C_{2-6}$-alkynyl or $C_{3-6}$-cycloalkyl, each of the $C_{1-6}$-alkyl, $-OC_{1-6}$-alkyl, $C_{2-6}$-alkenyl, $C_{2-10}$-alkynyl and $C_{3-6}$-cycloalkyl optionally substituted with 1-5 substituents of $R^6$, in conjunction with any of the above or below embodiments.

In another embodiment, the invention provides compounds of Formula I wherein $R^4$ is CN, $C(O)R^9$, $-OC_{1-6}$-alkyl, $C_{1-4}$-alkylC(O)$R^9$, methyl, ethyl, propyl, isopropyl, cyclopropyl, butyl, isobutyl, tert-butyl, pentyl, neopentyl or $C_{1-4}$-alkyl-amino-$C_{1-4}$-alkyl or $C_{1-10}$-dialkylamino$C_{1-4}$-alkyl-, in conjunction with any of the above or below embodiments.

In another embodiment, the invention provides compounds of Formula I wherein $R^4$ is $-OC_{1-6}$-alkyl, $C_{1-4}$-alkylC(O)$R^9$, methyl, ethyl, propyl, isopropyl, cyclopropyl, butyl, isobutyl, pentyl or $C_{1-4}$-alkyl-amino-$C_{1-4}$-alkyl or $C_{1-4}$-dialkylamino$C_{1-4}$-alkyl-, in conjunction with any of the above or below embodiments.

In another embodiment, the invention provides compounds of Formula I wherein wherein $R^4$ is methyl, ethyl, propyl, isopropyl, cyclopropyl, butyl, isobutyl, tert-butyl, pentyl or neopentyl, in conjunction with any of the above or below embodiments.

In another embodiment, the invention provides compounds of Formula I wherein wherein $R^4$ is methyl, ethyl, propyl, butyl, isobutyl or pentyl, in conjunction with any of the above or below embodiments.

In another embodiment, the invention provides compounds of Formula I wherein wherein $R^4$ is methyl, in conjunction with any of the above or below embodiments.

In another embodiment, the invention provides compounds of Formula I wherein $R^5$ is partially or fully saturated or fully unsaturated 3-6 membered monocyclic ring of carbon atoms optionally including 1-3 heteroatoms selected from O, N, or S, and optionally substituted independently with 1-5 substituents of $R^6$, in conjunction with any of the above or below embodiments.

In another embodiment, the invention provides compounds of Formula I wherein $R^5$ is phenyl, pyridyl, pyrimidyl, triazinyl, pyridazinyl, pyrazinyl, thiophenyl, furyl, pyrrolyl, pyrazolyl, imidazolyl, triazolyl, thiazolyl, oxazolyl, isoxazolyl, isothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, cyclopropyl, cyclobutyl, cyclopentyl, cyclohexyl or cycloheptyl, each of which is optionally substituted independently with 1-3 substituents of $R^6$, in conjunction with any of the above or below embodiments.

In another embodiment, the invention provides compounds of Formula I wherein $R^5$ is phenyl, pyridyl, pyrimidyl, triazinyl, pyridazinyl, pyrazinyl, thiophenyl, furyl, pyrrolyl, pyrazolyl, imidazolyl, triazolyl, thiazolyl, oxazolyl, isoxazolyl, isothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, cyclopropyl, cyclobutyl, cyclopentyl, cyclohexyl or cycloheptyl, each of which is optionally substituted independently with 1-3 substituents of F, Cl, Br, $CF_3$, $-OCF_3$, $C_2F_5$, $-OC_2F_5$, $-OCH_3$, $-SCH_3$, $-NHCH_3$, $NO_2$, $NH_2$, OH, CN, methyl, ethyl or propyl, in conjunction with any of the above or below embodiments.

In another embodiment, the invention provides compounds of Formula I wherein $R^5$ is phenyl, pyridyl, pyrimidyl, pyridazinyl, pyrazinyl, thiophenyl, furyl, pyrrolyl, pyrazolyl, imidazolyl, thiazolyl, oxazolyl, isoxazolyl or isothiazolyl, each of which is optionally substituted independently with 1-3 substituents of F, Cl, Br, $CF_3$, $C_2F_5$, $-OC_2F_5$, $-OCH_3$, —SCH$_3$, —NHCH$_3$, NO$_2$, NH$_2$, OH, CN, methyl, ethyl or propyl, in conjunction with any of the above or below embodiments.

In another embodiment, the invention provides compounds of Formula I wherein R$^5$ is phenyl, pyridyl, pyrimidyl, pyridazinyl, pyrazinyl or thiophenyl, each of which is optionally substituted independently with 1-3 substituents of F, Cl, Br, OH, CN or methyl, in conjunction with any of the above or below embodiments.

In another embodiment, the invention provides compounds of Formula I wherein R$^5$ is phenyl or pyridyl optionally substituted independently with 1-3 substituents of R$^6$, in conjunction with any of the above or below embodiments.

In another embodiment, the invention provides compounds of Formula I wherein R$^5$ is phenyl optionally substituted independently with 1-3 substituents of F, Cl, Br, OH, CN or methyl, in conjunction with any of the above or below embodiments.

In another embodiment, the invention provides compounds of Formula I wherein W is O, S, NH or NCH$_3$, in conjunction with any of the above or below embodiments.

In another embodiment, the invention provides compounds of Formula I wherein W is O, S or NH, in conjunction with any of the above or below embodiments.

In another embodiment, the invention provides compounds of Formula I wherein W is O, NH or NCH$_3$, in conjunction with any of the above or below embodiments.

In another embodiment, the invention provides compounds of Formula I wherein W is NH or NCH$_3$, in conjunction with any of the above or below embodiments.

In another embodiment, the invention provides compounds of Formula I wherein W is NH, in conjunction with any of the above or below embodiments.

In another embodiment, the invention provides compounds of Formula I wherein W is O or S, in conjunction with any of the above or below embodiments.

In another embodiment, the invention provides compounds of Formula I wherein W is O, in conjunction with any of the above or below embodiments.

In another embodiment, the invention provides compounds of Formula I wherein W is S, in conjunction with any of the above or below embodiments.

In another embodiment, the invention provides compounds of Formula I wherein X is O or S, in conjunction with any of the above or below embodiments.

In another embodiment, the invention provides compounds of Formula I wherein X is O, in conjunction with any of the above or below embodiments.

In another embodiment, the invention provides compounds of Formula I wherein X is S, in conjunction with any of the above or below embodiments.

In another embodiment, the invention provides compounds of Formula I wherein

R$^1$ is phenyl, pyridyl, pyrimidyl, triazinyl, pyridazinyl, pyrazinyl, thiophenyl, furyl, tetrahydrofuryl, pyrrolyl, tetrahydropyrrolyl, pyrazolyl, imidazolyl, triazolyl, tetrazolyl, thiazolyl, oxazolyl, oxazolinyl, isoxazolyl, isoxazolinyl, oxadiazolyl, isothiazolyl, morpholinyl, piperidinyl, piperazinyl, pyranyl, cyclopropyl, cyclobutyl, cyclopentyl or cyclohexyl, each of which is optionally substituted with 1-5 substituents of R$^6$;

each of R$^2$ and R$^3$, independently, is H, halo, haloalkyl or C$_{1-4}$-alkyl;

R$^4$ is CN, C(O)R$^6$, —OC$_{1-6}$-alkyl, C$_{1-4}$-alkylC(O)R$^6$, methyl, ethyl, propyl, isopropyl, cyclopropyl, butyl, isobutyl, tert-butyl, pentyl, neopentyl or C$_{1-4}$-alkyl-amino-C$_{1-4}$-alkyl or C$_{1-10}$-dialkylaminoC$_{1-4}$-alkyl-;

R$^5$ is a ring selected from phenyl, pyridyl, pyrimidyl, triazinyl, pyridazinyl, pyrazinyl, thiophenyl, furyl, pyrrolyl, pyrazolyl, imidazolyl, triazolyl, thiazolyl, oxazolyl, isoxazolyl, isothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, cyclopropyl, cyclobutyl, cyclopentyl, cyclohexyl and cycloheptyl, wherein said ring is optionally substituted independently with 1-3 substituents of R$^6$;

each R$^6$, independently, is H, F, Cl, Br, I, CF$_3$, C$_2$F$_5$, CN, OH, NO$_2$, NH$_2$, acetyl, oxo, C$_{1-6}$-alkyl, C$_{2-6}$-alkenyl, C$_{2-6}$-alkynyl, C$_{3-6}$-cycloalkyl, C$_{1-6}$-alkylamino-, C$_{1-6}$-dialkylamino-, C$_{1-6}$-alkoxyl, C$_{1-6}$-thioalkoxyl or —SO$_2$C$_{1-6}$-alkyl;

W is O, S or NH; and

X is O.

In another embodiment, the invention provides compounds of Formula I wherein

R$^1$ is C$_{1-6}$-alkyl, —OC$_{1-6}$-alkyl, —SC$_{1-6}$-alkyl, —NHC$_{1-6}$-alkyl or a ring selected from phenyl, pyridyl, pyrimidyl, pyridazinyl, pyrazinyl, thiophenyl, furyl, tetrahydrofuryl, pyrrolyl, tetrahydropyrrolyl, pyrazolyl, imidazolyl, triazolyl, thiazolyl, oxazolyl, isoxazolyl, isothiazolyl, morpholinyl, piperidinyl, piperazinyl, cyclopropyl, cyclobutyl, cyclopentyl or cyclohexyl, each of C$_{1-6}$-alkyl, —OC$_{1-6}$-alkyl, —SC$_{1-6}$-alkyl, —NHC$_{1-6}$-alkyl and ring optionally substituted with 1-5 substituents of R$^6$;

each of R$^2$ and R$^3$, independently, is H, F, Cl, CF$_3$, methyl or ethyl;

R$^4$ is CN, C(O)R$^6$, —OC$_{1-6}$-alkyl, C$_{1-4}$-alkylC(O)R$^6$, methyl, ethyl, propyl, isopropyl, cyclopropyl, butyl, isobutyl, tert-butyl, pentyl, C$_{1-4}$-alkyl-amino-C$_{1-4}$-alkyl or C$_{1-4}$-dialkylaminoC$_{1-4}$-alkyl-;

R$^5$ is a ring selected from phenyl, pyridyl, pyrimidyl, triazinyl, pyridazinyl, pyrazinyl, thiophenyl, furyl, pyrrolyl, pyrazolyl, imidazolyl, triazolyl, thiazolyl, oxazolyl, isoxazolyl, isothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, cyclopropyl, cyclobutyl, cyclopentyl, cyclohexyl and cycloheptyl, wherein said ring is optionally substituted independently with 1-3 substituents of R$^6$;

each R$^6$, independently, is H, F, Cl, Br, I, CF$_3$, C$_2$F$_5$, CN, OH, NO$_2$, NH$_2$, acetyl, oxo, C$_{1-6}$-alkyl, C$_{2-6}$-alkenyl, C$_{2-6}$-alkynyl, C$_{3-6}$-cycloalkyl, C$_{1-6}$-alkylamino-, C$_{1-6}$-dialkylamino-, C$_{1-6}$-alkoxyl or C$_{1-6}$-thioalkoxyl;

W is O, S or NH; and

X is O.

In another embodiment, the invention provides compounds of Formula I wherein R$^1$ is phenyl, pyridyl, pyrimidyl, pyridazinyl, pyrazinyl, thiophenyl, furyl, pyrrolyl, pyrazolyl, imidazolyl, triazolyl, thiazolyl, oxazolyl, oxazolinyl, isoxazolyl, isoxazolinyl, oxadiazolyl or isothiazolyl, each of which is optionally substituted independently with 1-3 substituents of R$^6$;

each of R$^2$ and R$^3$, independently, is H, F, Cl, CF$_3$ or methyl;

R$^4$ is CN, —C(O)methyl, —OC$_{1-6}$-alkyl, C$_{1-4}$-alkylC(O)R$^7$, methyl, ethyl, propyl, isopropyl, butyl, pentyl, C$_{1-4}$-alkyl-amino-C$_{1-4}$-alkyl or C$_{1-4}$-dialkylaminoC$_{1-4}$-alkyl-;

R$^5$ is a ring selected from phenyl, pyridyl, pyrimidyl, triazinyl, pyridazinyl, pyrazinyl, thiophenyl, furyl, pyrrolyl, pyrazolyl, imidazolyl, triazolyl, thiazolyl, oxazolyl, isoxazolyl and isothiazolyl, wherein said ring is optionally substituted independently with 1-3 substituents of R$^6$;

each R$^6$, independently, is H, F, Cl, Br, CF$_3$, —OCF$_3$, C$_2$F$_5$, —O—C$_{1-3}$-alkyl, —S—C$_{1-3}$-alkyl, —NH—C$_{1-3}$-alkyl, NO$_2$, NH$_2$, OH, CN, methyl, ethyl propyl or isopropyl;

W is O or NH; and

X is O.

In another embodiment, the invention provides compounds of Formula I, and pharmaceutically acceptable salts thereof, selected from 8-(2,4-difluorophenyl)-3-(2,4-difluorophenylamino)-1-methylpyrido[3,2-d]pyridazin-2(1H)-one;
8-(2,4-difluorophenyl)-3-(4-fluorophenoxy)-1-methylpyrido[3,2-d]pyridazin-2(1H)-one; and
3-(2,4-difluorophenylamino)-8-(2-fluoro-4-(trifluoromethyl)phenyl)-1-methylpyrido[3,2-d]pyridazin-2(1H)-one.

In another embodiment, the invention provides the compound 8-(2,4-difluorophenyl)-3-(2,4-difluorophenylamino)-1-methylpyrido[3,2-d]pyridazin-2(1H)-one, or a pharmaceutically acceptable salt form thereof.

In another embodiment, the invention provides the compound 8-(2,4-difluorophenyl)-3-(4-fluorophenoxy)-1-methylpyrido[3,2-d]pyridazin-2(1H)-one, or a pharmaceutically acceptable salt form thereof.

In another embodiment, the invention provides the compound 3-(2,4-difluorophenylamino)-8-(2-fluoro-4-(trifluoromethyl)phenyl)-1-methylpyrido[3,2-d]pyridazin-2(1H)-one, or a pharmaceutically acceptable salt form thereof.

In another embodiment, the invention provides a compound of Formula I-B

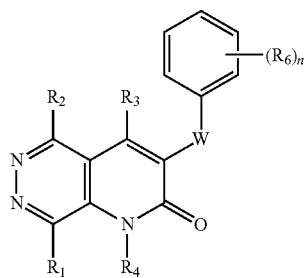

I-B or a pharmaceutically acceptable salt thereof, wherein
$R^1$ is $C_{1-8}$-alkyl, —$OC_{1-8}$-alkyl, —$SC_{1-8}$-alkyl, —$NHC_{1-8}$-alkyl, —$N(C_{1-8}$-alkyl$)_2$, $C_{2-8}$-alkenyl, $C_{2-8}$-alkynyl or $C_{3-8}$-cycloalkyl, each of which is optionally substituted with 1-5 substituents of $R^6$,
or $R^1$ is a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with 1-5 substituents of $R^6$;
each of $R^2$ and $R^3$, independently, is H, halo, haloalkyl, $NO_2$, CN, $C_{1-6}$-alkyl, $C_{1-6}$-alkoxyl or $C_{1-6}$-aminoalkyl;
$R^4$ is CN, C(O)$R^6$, $C_{1-6}$-alkyl, —$OC_{1-6}$-alkyl, $C_{2-6}$-alkenyl, $C_{2-6}$-alkynyl or $C_{3-6}$-cycloalkyl;
each $R^6$, independently, is F, Cl, Br, I, $CF_3$, $C_2F_5$, CN, OH, $NO_2$, $NH_2$, acetyl, oxo, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, —$SO_2C_{1-6}$-alkyl or a saturated or partially or fully unsaturated 5-6 membered monocyclic ring formed of carbon atoms optionally including 1-3 heteroatoms selected from O, N, or S and optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine or diisopropylamine;
n is 0, 1, 2, 3, 4 or 5; and
W is O, S or NH.

In another embodiment, the invention provides a compound of Formula I-C,

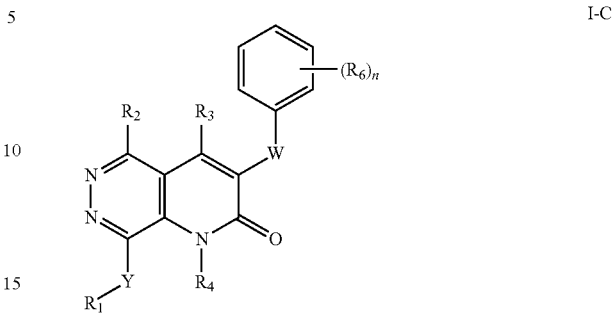

I-C or a pharmaceutically acceptable salt thereof, wherein
Y is absent or Y is O, S or NH;
$R^1$ is $C_{1-8}$-alkyl or $R^1$ is a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said ring system and is $C_{1-8}$-alkyl optionally substituted independently with 1-5 substituents of $R^6$;
each of $R^2$ and $R^3$, independently, is H, halo, haloalkyl, $NO_2$, CN, $C_{1-6}$-alkyl, $C_{1-6}$-alkoxyl or $C_{1-6}$-aminoalkyl;
$R^4$ is CN, C(O)$R^6$, $C_{1-6}$-alkyl, —$OC_{1-6}$-alkyl, $C_{2-6}$-alkenyl, $C_{2-6}$-alkynyl or $C_{3-6}$-cycloalkyl;
each $R^6$, independently, is F, Cl, Br, I, $CF_3$, $C_2F_5$, CN, OH, $NO_2$, $NH_2$, acetyl, oxo, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, —$SO_2C_{1-6}$-alkyl or a saturated or partially or fully unsaturated 5-6 membered monocyclic ring formed of carbon atoms optionally including 1-3 heteroatoms selected from O, N, or S and optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine or diisopropylamine;
n is 0, 1, 2, 3, 4 or 5; and
W is O, S or NH.

In another embodiment, the invention provides a compound of Formula I-D,

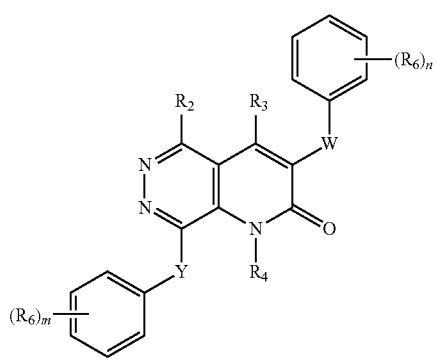

I-D or a pharmaceutically acceptable salt thereof, wherein
Y is absent or Y is O, S or NH;
each of $R^2$ and $R^3$, independently, is H, halo, haloalkyl, $NO_2$, CN, $C_{1-6}$-alkyl, $C_{1-6}$-alkoxyl or $C_{1-6}$-aminoalkyl;

$R^4$ is CN, $C(O)R^6$, $C_{1-6}$-alkyl, —$OC_{1-6}$-alkyl, $C_{2-6}$-alkenyl, $C_{2-6}$-alkynyl or $C_{3-6}$-cycloalkyl;

each $R^6$, independently, is F, Cl, Br, I, $CF_3$, $C_2F_5$, CN, OH, $NO_2$, $NH_2$, acetyl, oxo, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, —$SO_2C_{1-6}$-alkyl or a saturated or partially or fully unsaturated 5-6 membered monocyclic ring formed of carbon atoms optionally including 1-3 heteroatoms selected from O, N, or S and optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine or diisopropylamine;

m is 0, 1, 2, 3, 4 or 5;

n is 0, 1, 2, 3, 4 or 5; and

W is O, S or NH.

In yet another embodiment, the compounds of Formulas I, I-B, I-C and I-D include each individual example, and each and every pharmaceutically acceptable salt form thereof, described hereinbelow.

DEFINITIONS

The following definitions should assist in understanding the invention described herein.

The term "comprising" is meant to be open ended, including the indicated component(s), but not excluding other elements.

The term "$C_{\alpha-\beta}$alkyl", when used either alone or within other terms such as "haloalkyl" and "alkylamino", embraces linear or branched radicals having $\alpha$ to $\beta$ number of carbon atoms (such as $C_1$-$C_{10}$). Examples of such radicals include methyl, ethyl, n-propyl, isopropyl, n-butyl, isobutyl, sec-butyl, tert-butyl, pentyl, isoamyl, hexyl and the like. The term "alkylenyl" embraces bridging divalent alkyl radicals such as methylenyl and ethylenyl.

The term "alkenyl", when used alone or in combination, embraces linear or branched radicals having at least one carbon-carbon double bond in a moiety having between two and ten carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "alkynyl", when used alone or in combination, denotes linear or branched radicals having at least one carbon-carbon triple bond and having two to ten carbon atoms. Examples of such radicals include, without limitation, ethynyl, propynyl (propargyl), butynyl, and the like.

The term "alkoxy" or "alkoxyl", when used alone or in combination, embraces linear or branched oxygen-containing radicals each having alkyl portions of one or more carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. Unless otherwise specified, the "aryl" group may be substituted, such as with 1 to 5 substituents including lower alkyl, hydroxyl, halo, haloalkyl, nitro, cyano, alkoxy and lower alkylamino, and the like. Phenyl substituted with —O—$CH_2$—O— or —O—$CH_2$—$CH_2$—O— forms an aryl benzodioxolyl substituent.

The term "carbocyclic", also referred to herein as "cycloalkyl", when used alone or in combination, means a partially or fully saturated ring moiety containing one ("monocyclic"), two ("bicyclic") or even three ("tricyclic") rings wherein such rings may be attached together in a fused manner and formed from carbon atoms. Examples of saturated carbocyclic radicals include saturated 3 to 6-membered monocyclic groups such as cyclopropane, cyclobutane, cyclopentane and cyclohexane and partially saturated monocyclic groups such as cyclopentene, cyclohexene or cyclohexadiene. The partially saturated groups are also encompassed in the term "cycloalkenyl" as defined below.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that the ring, at the point of attachment, is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents.

Thus, the term "a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted" refers to a single ring or multiple ring system comprising the delineated number of atoms, the atoms being carbon or, where indicated, a heteroatom such as nitrogen (N), oxygen (O) or sulfur (S). Where the number of atoms is not delineated, such as a "monocyclic ring system" or a "bicyclic ring system", the numbers of atoms are 3-8 for a monocyclic and 6-12 for a bicyclic ring. The ring or ring system may contain substitutents thereon, attached at any atom that allows a stable compound to be formed.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, aza-quinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heteroaryl" also embraces bicyclic radicals wherein 5- or 6-membered heteroaryl radicals are fused/condensed with aryl radicals or unsaturated condensed heterocyclic groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of partially saturated and saturated heterocyclyl include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-azafluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "aminocarbonyl" denotes an amide group of the formula —C(=O)NH$_2$.

The terms "alkylthio" and "thioalkoxyl" embrace radicals containing a linear or branched alkyl radical, of one to ten carbon atoms, attached to a divalent sulfur atom. An example of "alkylthio" is methylthio, (CH$_3$S—).

The term "Formula I" includes any sub formulas, such as Formulas I-B and I-C.

The term "pharmaceutically-acceptable" when used with reference to a compound of Formulas I, I-B, I-C and I-D is intended to refer to a form of the compound that is safe for administration. For example, a free base, a salt form, a solvate, a hydrate, a prodrug or derivative form of a compound of Formula I, I-B, I-C or I-D, which has been approved for mammalian use, via oral ingestion or any other route of administration, by a governing body or regulatory agency, such as the Food and Drug Administration (FDA) of the United States, is pharmaceutically acceptable.

Included in the compounds of Formulas I, I-B, I-C and I-D are the pharmaceutically acceptable salt forms of the free-base compounds. The term "pharmaceutically-acceptable salts" embraces salts, commonly used to form alkali metal salts and to form addition salts of free acids or free bases, which have been approved by a regulatory agency. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I, I-B, I-C and I-D may be prepared from an inorganic acid or from an organic acid. Examples of such inorganic acids are hydrochloric, hydrobromic, hydroiodic, hydrofluoric, nitric, carbonic, sulfonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I and II include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I, I-B, I-C and I-D.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid (HCl), hydrobromic acid (HBr), citric acid, sulphuric acid and phosphoric acid and such organic acids as oxalic acid, stearic and, salicylic acid, pamoic acid, gluconic acid, ethanesulfonic acid, methanesulfonic acid (MSA), benzenesulfonic acid (BSA), toluenesulfonic acid, tartaric acid, fumaric acid, medronic acid, napsylic acid, maleic acid, succinic acid and citric acid. Other examples include salts with alkali metals or alkaline earth metals such as sodium, potassium, calcium or magnesium, or with organic bases.

Additional examples of such salts can be found in Berge et al., J. Pharm. Sci., 66, 1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is broadly construed herein, and intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate a kinase enzyme.

The term "pharmaceutically-acceptable derivative" as used herein, denotes a derivative, which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formulas I, I-B, I-C and I-D. A "pharmaceutically-acceptable prodrug" as used herein, denotes a prodrug, which is pharmaceutically acceptable. Pharmaceutically acceptable modifications to the compounds of Formula I are readily appreciated by those of ordinary skill in the art.

The compound(s) of Formulas I, I-B, I-C and I-D may be used to treat a subject by administering the compound(s) as a pharmaceutical composition. To this end, the compound(s) can be combined with one or more carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies.

The term "leaving groups" (also denoted as "LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I, I-B, I-C and I-D. The compounds of Formulas I, I-B, I-C and I-D can be synthesized according to the procedures described in the following Scheme 1 (corresponding to general Method A, respectively), wherein the substituents are as defined for Formulas I, I-B, I-C and I-D, above, except where further noted. The synthetic methods described below are merely exemplary, and the compounds of the invention may also be synthesized by alternate routes as appreciated by persons of ordinary skill in the art.

The following list of abbreviations used throughout the specification represent the following and should assist in understanding the invention:
ACN, MeCN—acetonitrile
BSA—bovine serum albumin
BOP—benzotriazol-1-yl-oxy hexafluorophosphate
$Br_2$—bromine
CDI—carbonyldiimidazole
$Cs_2CO_3$—cesium carbonate
$CHCl_3$—chloroform
$CH_2Cl_2$, DCM—dichloromethane, methylene chloride
DCC—dicyclohexylcarbodiimide
DIC—1,3-diisopropylcarbodiimide
DIEA, DIPEA—diisopropylethylamine
DME—dimethoxyethane
DMF—dimethylformamide
DMAP—4-dimethylaminopyridine
DMSO—dimethylsulfoxide
EDC—1-(3-dimethylaminopropyl)-3-ethylcarbodiimide
$Et_2O$—diethyl ether
EtOAc—ethyl acetate
G, g, gm—gram
h, hr—hour
$H_2$—hydrogen
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
LG—leaving group
$MgSO_4$—magnesium sulfate
MS—mass spectrum
MeOH—methanol
$N_2$—nitrogen
$NaCNBH_3$—sodium cyanoborohydride
$Na_2CO_3$—sodium carbonate
$NaHCO_3$—sodium bicarbonate
NaH—sodium hydride
$NaOCH_3$—sodium methoxide
NaOH—sodium hydroxide
$Na_2SO_4$—sodium sulfate
NBS—N-bromosuccinimide
$NH_4Cl$—ammonium chloride
$NH_4OH$—ammonium hydroxide
NMP—N-methylpyrrolidinone
$P(t-bu)_3$—tri(tert-butyl)phosphine
PBS—phospate buffered saline
Pd/C—palladium on carbon
$Pd(PPh_3)_4$—palladium(0)triphenylphosphine tetrakis
$Pd(dppf)Cl_2$—palladium(1,1-bisdiphenylphosphinoferrocene) II chloride
$Pd(OAc)_2$—palladium acetate
PyBop—benzotriazol-1-yl-oxy-tripyrrolidino-phosphonium hexafluorophosphate
RT, rt—room temperature
TBTU—O-benzotriazol-1-yl-N,N,N',N'-tetramethyluronium tetrafluoroborate
TEA, $Et_3N$—triethylamine
TFA—trifluoroacetic acid
THF—tetrahydrofuran
UV—ultraviolet light

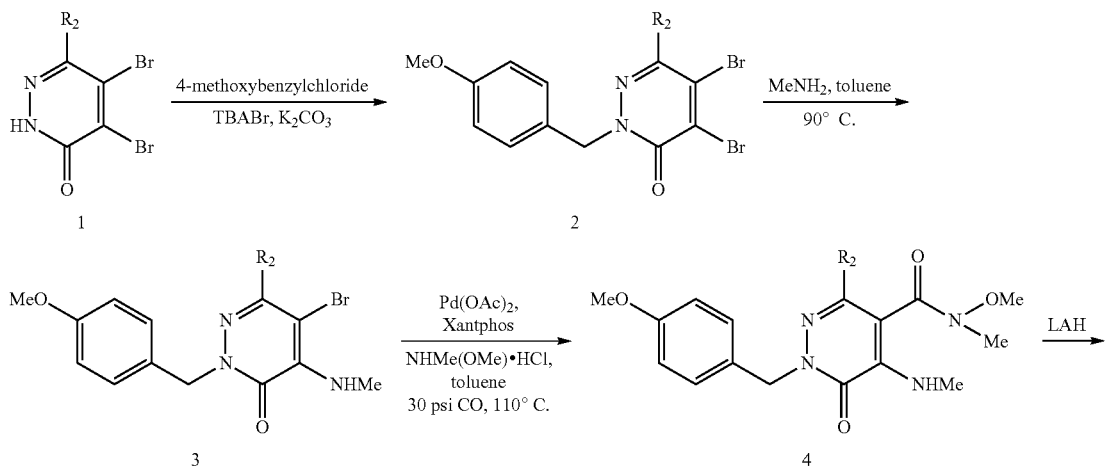

Scheme 1 (Method A)

-continued

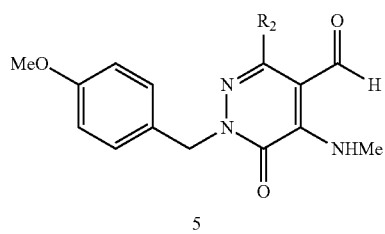
5

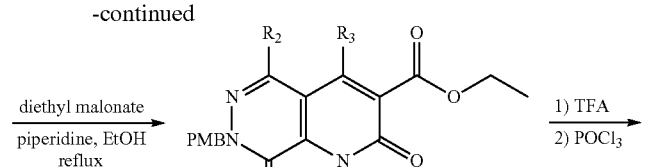

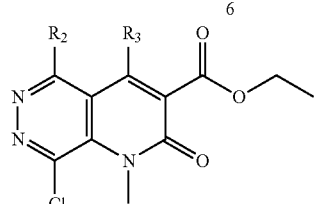
7

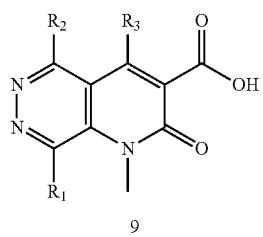
9

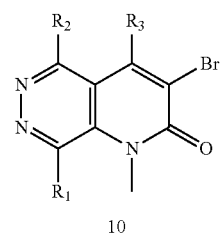
10

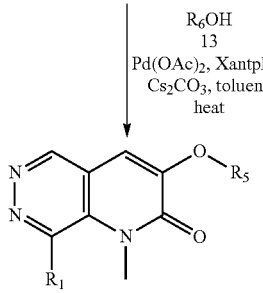
14

Amino-linked pyridazino-pyridinones 12 and ether-linked pyridazino-pyridinones 14, (Formula I; W=NH and W=—O—) as shown in scheme 1 linking ring moiety $R^5$ (generally referred to herein throughout the specification as the "B" ring) to the pyridazino-pyridinone core may be made by the methods generally described in Scheme 1, also designated herein as Methods A (compounds 12 and compounds 14). As shown, a desirable $R^2$ substituted dibromo pyridazinone 1 may be reacted with 4-methoxybenzylbromide in the presence of tetrabytulammonium bromide and a unable base, such as a carbonate base, for instance potassium carbonate as shown, to afford the alkylated adduct 2. One bromide of compound 2 may be selectively aminated with methyl amine under suitable reaction conditions such as toluene and heat as shown, to produce the amino methylpyridazinone intermediate 3. The other bromide of pyridazinone 3 can be converted to the corresponding weinreb amide 4 under conditions shown above, and subsequently reduces with the corresponding aldehyde 5 with a suitable reducing agent, such as a strong base, such as LAH as shown. Aldehyde 5 may be connected to the corresponding ester 6 using the appropriate malonate as shown. Note that this method affords compounds where $R^4$ is methyl. Similar procedures may be employed to produce compound of Formulas I wherein $R^4$ is other alkyl moieties, such as ethyl, propyl, butyl, isopropyl, pentyl and the like.

The para-methoxybenzyl protecting group of intermediate 6 can be removed with an acid, such as TFA, followed by conversion of the ketone on compound 6 to the corresponding chloride 7 using conventional methods, such as phosphorus oxychloride under suitable conditions. The chloride of intermediate 7 can then be reacted with an aromatic boronic acid 8 to install a desired aromatic $R^1$ group to afford intermediate 9, under Suzuki or Suzuki-like reaction conditions, which are generally known in the art, and which are briefly described hereinbelow. Note that the work-up of a Suzuki or like reaction generally employs use of a base, which base also serves to hydrolyze the ester in 7 to the corresponding acid 9. The acid of compound 9 can be converted to the corresponding bromide 10 using conventional methods, such as with a suitable brominating agent such as NBS under suitable conditions, as those shown above. The bromine adduct 10 can be subjected to a suitable nucleophile, such as a primary or secondary amine 11 (shown above with a priomary amine) under suitable coupling conditions, such as those shown in scheme 1, to afford the desired substituted pyridazino-pyridinone 12.

Similarly, compounds 14 where W=O (or S) can also be made by conventional methods known to one skilled in the art. One method, as illustrated above, involves reacting bromide intermediate 10 with a desired alcohol 13 in the presence of a suitable palladium catalyst and cesium carbonate and xanthphos to afford ether linked compounds 14 of formula I.

The boronic ester intermediates 8 may be prepared by methods described in the following references: (1) PCT Int. Patent Appl. No. WO 2005073189, titled "Preparation of fused heteroaryl derivatives as p38 kinase inhibitors" or (2) PCT Int. Patent Appl. No. WO 2006094187, titled "Preparation of phthalazine, aza- and diaza-phthalazine compounds as protein kinase, especially p38 kinase, inhibitors for treating inflammation and related conditions", both publications of which are hereby incorporated herein by reference in their entirety.

The Suzuki method is a reaction using a borane reagent, such as a dioxaborolane intermediate 8 (also described in scheme 3 below as a borane B-A intermediate 8), and a suitable leaving group containing reagent, such as the Br-pyridazino-pyridinone 7 (Br is a suitable halogen leaving group "LG"). As appreciated to one of ordinary skill in the art, Suzuki reactions also utilize a palladium catalyst. Suitable palladium catalysts include $Pd(PPh_3)_4$, $Pd(OAc)_2$ or $Pd(dppf)Cl_2$. Where LG is a halide, the halide may be an iodide, a bromide or even a chloride (chloro-pyridyl or chloro-picolinyl B rings undergo Suzuki reactions in the presence of $Pd(OAc)_2$). Other LGs are also suitable. For example, Suzuki couplings are known to occur with a sulfonate, such as trifluoromethanesulfonate, as the leaving group.

The Suzuki reaction conditions may vary. For example, Suzuki reactions are generally run in the presence of a suitable base such as a carbonate base, bicarbonate or an acetate base, in a suitable solvent such as toluene, acetonitrile, DMF or an aqueous-organic solvent combination or a biphasic system of solvents. Further, the reaction may require heat depending upon the particular pyradazino-pyridinone 7 and/or boronic acid or ester 8, as appreciated by those skilled in the art. In addition, where the B ring is an aromatic moiety, such as phenyl, the reaction may be complete in a short period of time with heat.

Other methods of installing the boronate on a desired aromatic ring are known. For example metal coupling chemistry, such Stille, Kumada, Negishi coupling methods, and the like, may be employed to the pyridazino-pyridinone cores 7 to prepare desired cyclic B-ring-substituted intermediates.

To enhance the understanding and appreciation of the present invention, the following specific examples (starting reagents, intermediates and compounds of Formulas I, I-B and I-C, and I-D and methods of making compounds of the invention are set forth. It should be appreciated that the above general methods and specific examples below are merely for illustrative purposes only and are not to be construed as limiting the scope of this invention in any manner. The following analytical methods were used to purify and/or characterize the compounds, and intermediates, described in the examples below.

Analytical Methods:

Unless otherwise indicated, all HPLC analyses were run on a Agilent Model 1100 system with an Agilent Technologies Zorbax SB-$C_8$(5μ) reverse phase column (4.6×150 mm; Part no. 883975-906) run at 30° C. with a flow rate of about 1.50 mL/min. The mobile phase used solvent A ($H_2O$/0.1% TFA) and solvent B (ACN/0.1% TFA) with a 11 min gradient from 5% to 100% ACN. The gradient was followed by a 2 min. return to 5% ACN and about a 2.5 min. re-equilibration (flush).

LC-MS Method:

Samples were run on an Agilent model-1100 LC-MSD system with an Phenomenex Synergi MAX-RP (4.0μ) reverse phase column (2×50 mm) at 40° C. The flow rate was constant and ranged from about 0.75 mL/min to about 1.0 mL/min.

The mobile phase used a mixture of solvent A ($H_2O$/0.1% TFA) and solvent B (ACN/0.1% TFA) with a 5 min time period for a gradient from 10% to 100% solvent B. The gradient was followed by a 0.5 min period to return to 10% solvent B and a 1.5 min 10% solvent B re-equilibration (flush) of the column.

Preparative HPLC Method:

Where indicated, compounds of interest were purified via reverse phase HPLC using a Gilson workstation utilizing one of the following two columns and methods: (A) Using a 50×100 mm column (Waters, Externa, C18, 5 microns) at 50 mL/min. The mobile phase used was a mixture of solvent A ($H_2O$/10 mM ammonium carbonate at pH about 10, adjusted with conc. $NH_4OH$) and solvent B (85:15 ACN/water, 10 mM ammonium carbonate at pH of about 10 adjusted with conc. $NH_4OH$). Each purification run utilized a 10 minute gradient from 40% to 100% solvent B followed by a 5 minute flow of 100% solvent B. The gradient was followed by a 2 min return to 40% solvent B. (B) Using a 20×50 mm column at 20 mL/min. The mobile phase used was a mixture of solvent A ($H_2O$/0.1% TFA) and solvent B (ACN/0.1% TFA) with a 10 min gradient from 5% to 100% solvent B. The gradient is followed by a 2 min return to 5% ACN.

Proton NMR Spectra:

Unless otherwise indicated, all $^1H$ NMR spectra were run on a Varian series Mercury 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an $(M+H^+)$ molecular ion. The molecular ion reported was obtained by electrospray detection method. Compounds having an isotopic atom, such as bromine and the like, are reported according to the detected isotopic pattern, as appreciated by those skilled in the art.

EXAMPLE 1

Via Method A

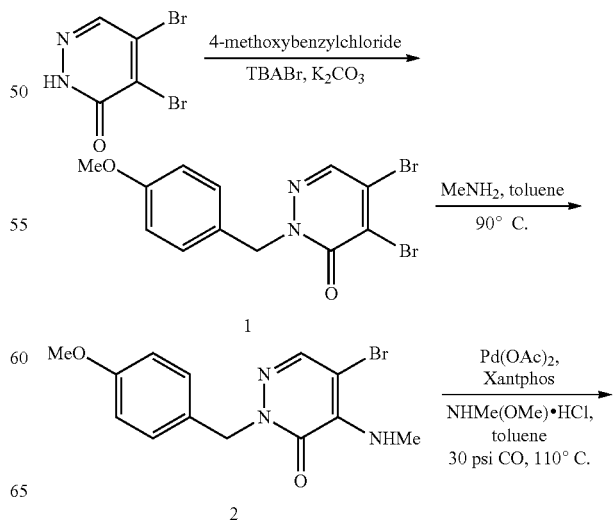

-continued

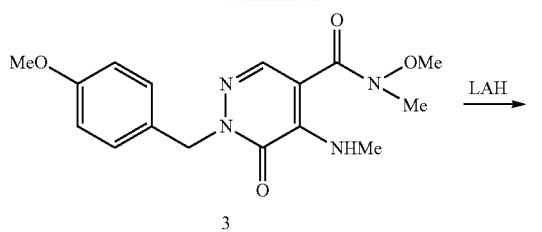
3

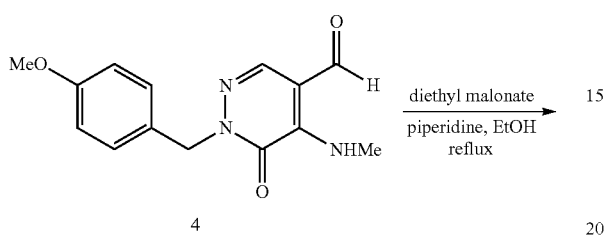
4

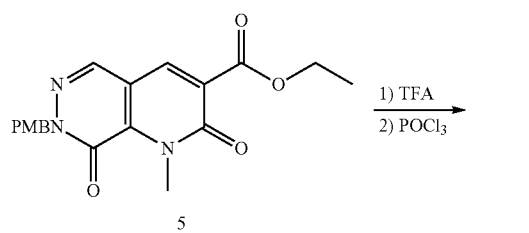
5

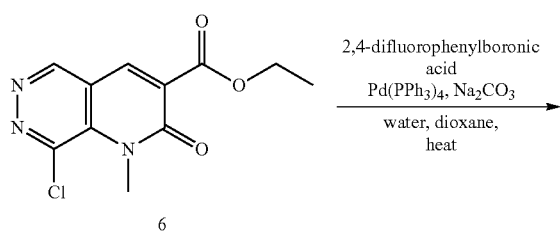
6

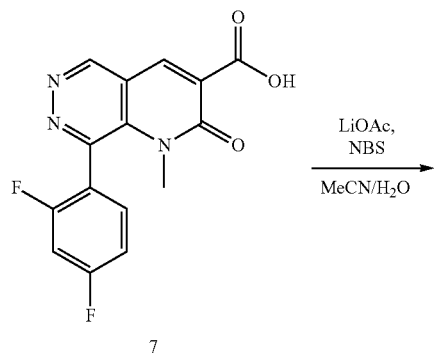
7

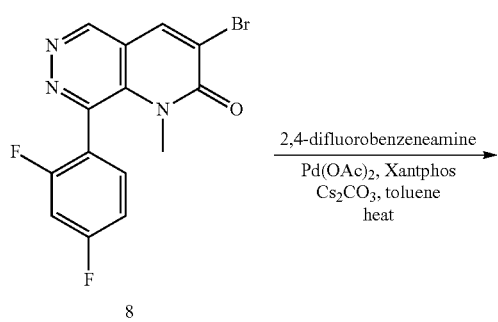
8

-continued

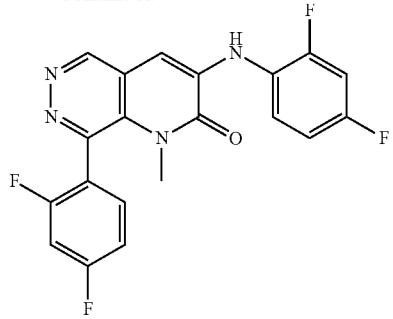
9

Synthesis of 8-(2,4-Difluorophenyl)-3-(2,4-difluorophenylamino)-1-methylpyrido[3,2-d]pyridazin-2(1H)-one (9)

Step 1: 2-(4-Methoxybenzyl)-4,5-dibromopyridazin-3(2H)-one (1)

A mixture of 4,5-dibromopyridazinone (25 g, 98 mmol), anhydrous potassium carbonate (34 g, 246 mmol), 4-methoxybenzylchloride (14 mL, 103 mmol) and tetrabutylammonium bromide (1.6 g, 4.9 mmol) in $CH_3CN$ (200 mL) was stirred at 45° C. for 3 h and then at 80° C. for 2 h. The mixture was allowed to cool to 22° C. and filtered through a pad of Celite. The pad was washed with $CH_2Cl_2$, followed by EtOAc, and the combined filtrate was evaporated to dryness. The crude product was suspended in MeOH and sonicated. The solid was collected by suction filtration, washed with MeOH, and air-dried to give 2-(4-methoxybenzyl)-4,5-dibromopyridazin-3(2H)-one as a brown solid. The filtrate was concentrated and purified by silica gel chromatography, eluting with 20% hexane in $CH_2Cl_2$, to give 2-(4-methoxybenzyl)-4,5-dibromopyridazin-3(2H)-one as a pale yellow solid.
$^1H$ NMR (400 MHz, $CDCl_3$) @ ppm 3.78 (s, 3H), 5.25 (s, 2H), 6.85 (d, J=8.53 Hz, 2H), 7.40 (d, J=9.03 Hz, 2H), 7.78 (s, 1H).

Step 2: 2-(4-Methoxybenzyl)-5-bromo-4-(methylamino)pyridazin-3(2H)-one (2)

In a glass pressure reactor vessel equipped with a magnetic stir bar, toluene (100 mL) was saturated with anhydrous methylamine at 0° C. then 2-(4-methoxybenzyl)-4,5-dibromopyridazin-3(2H)-one (1) (22 g, 59 mmol) was added. The vessel was sealed and the suspension was stirred and heated at 90° C. for 18 h. The resulting suspension was allowed to cool to RT. Anhydrous methylamine was bubbled through the mixture for 15 min, the reactor was sealed again, and the mixture was stirred and heated at 90° C. for an additional 18 h. After cooling to RT, the mixture was concentrated in vacuo to dryness. The resulting brown solid was suspended in MeOH and sonicated. The solid was collected by suction filtration, washed with MeOH, and dried in vacuo to give 2-(4-methoxybenzyl)-5-bromo-4-(methylamino)pyridazin-3(2H)-one as a yellow solid.

MS (ESI, pos. ion) m/z: 324, 326 (M+1, M+3).

$^1H$ NMR (400 MHz, DMSO-$d_6$) ppm 3.18 (d, J=5.5 Hz, 3H), 3.72 (s, 3H), 5.09 (s, 2H), 6.83-6.97 (m, 3H), 7.23 (d, J=8.5 Hz, 2H), 7.69 (s, 1H).

Step 3: 1-(4-Methoxybenzyl)-N-methoxy-N-methyl-5-(methylamino)-6-oxo-1,6-dihydropyridazine-4-carboxamide (3)

A glass pressure vessel equipped with a CO regulator was charged with 2-(4-methoxybenzyl)-5-bromo-4-(methylamino)pyridazin-3(2H)-one (2) (7.0 g, 22 mmol), N,O-dimethylhydroxylamine hydrochloride (3.2 g, 32 mmol), potassium phosphate (14 g, 65 mmol), and toluene (60 mL). The mixture was purged with Ar then palladium (II) acetate (0.24 g, 1.1 mmol) and 4,5-bis(diphenylphosphino)-9,9-dimethylxanthene (Xantphos) (1.2 g, 2.2 mmol) were added. The vessel was sealed and charged with CO (30 psi) and the reaction mixture was stirred in a 110° C. oil bath behind a blast shield for 44 h. After cooling to room temperature, the reaction mixture was diluted with water and $CH_2Cl_2$. The bi-phasic mixture was filtered through a pad of Celite and the pad was washed with $CH_2Cl_2$. The organic layer was separated, dried over $Na_2SO_4$, filtered, and concentrated in vacuo to afford the crude product as a brown residue. The crude product was purified by silica gel chromatography, eluting with a gradient of 0-3% MeOH in $CH_2Cl_2$, to give 1-(4-methoxybenzyl)-N-methoxy-N-methyl-5-(methylamino)-6-oxo-1,6-dihydropyridazine-4-carboxamide as a yellow foam. MS (ESI, pos. ion) m/z: 333 (M+1). $^1$H NMR (400 MHz, DMSO-$d_6$) ppm 2.70 (d, J=5.5 Hz, 3H), 3.23 (s, 3H), 3.57 (s, 3H), 3.72 (s, 3H), 5.12 (s, 2H), 6.81-6.94 (m, 2H), 7.19-7.31 (m, 3H), 7.52 (s, 1H).

Step 4: 1-(4-Methoxybenzyl)-5-(methylamino)-6-oxo-1,6-dihydropyridazine-4-carbaldehyde (4)

A solution of 1-(4-methoxybenzyl)-N-methoxy-N-methyl-5-(methylamino)-6-oxo-1,6-dihydropyridazine-4-carboxamide (3) (4.60 g, 13.8 mmol) in THF (50.0 mL) was treated with 1.0 M LAH in THF (15 mL, 15 mmol) at −78° C. The mixture was stirred at 0° C. for 1 h then quenched carefully at 0° C. with MeOH (1.0 mL), followed by water (1.0 mL) and 1 M aq HCl (1.0 mL). The resulting suspension was filtered and the filtrate was concentrated in vacuo to give 1-(4-methoxybenzyl)-5-(methylamino)-6-oxo-1,6-dihydropyridazine-4-carbaldehyde as a pale yellow solid. MS (ESI, pos. ion) m/z: 274 (M+1).

Step 5: Ethyl 7-(4-methoxybenzyl)-1-methyl-2,8-dioxo-1,2,7,8-tetrahydropyrido[2,3-d]pyridazine-3-carboxylate (5)

A mixture of 1-(4-methoxybenzyl)-5-(methylamino)-6-oxo-1,6-dihydropyridazine-4-carbaldehyde (4) (3.78 g, 13.8 mmol), diethyl malonate (4.20 mL, 27.7 mmol), piperidine (1.44 mL, 14.5 mmol), and EtOH (100 mL) was stirred at reflux in an oil bath for 5 h. The reaction mixture was allowed to stand at RT for 18 h to afford a suspension. The solid was collected by suction filtration, washed with EtOH (10 mL), and dried in vacuo to afford ethyl 7-(4-methoxybenzyl)-1-methyl-2,8-dioxo-1,2,7,8-tetrahydropyrido[2,3-d]pyridazine-3-carboxylate as a tan solid. MS (ESI, pos. ion) m/z: 370 (M+1).
$^1$H NMR (400 MHz, DMSO-$d_6$) ppm 1.29 (t, J=7.0 Hz, 3H), 3.72 (s, 3H), 4.01 (s, 3H), 4.29 (q, J=7.1 Hz, 2H), 5.21 (s, 2H), 6.89 (d, J=8.6 Hz, 2H), 7.31 (d, J=8.6 Hz, 2H), 8.27 (s, 1H), 8.38 (s, 1H).

Step 6: Ethyl 8-chloro-1-methyl-2-oxo-1,2-dihydropyrido[3,2-d]pyridazine-3-carboxylate (6)

A solution of ethyl 7-(4-methoxybenzyl)-1-methyl-2,8-dioxo-1,2,7,8-tetrahydropyrido[2,3-d]pyridazine-3-carboxylate (5) (2.45 g, 6.63 mmol) in TFA (15 mL) was heated in a microwave at 125° C. for 150 min, then cooled to RT. The volatiles were removed in vacuo to give crude ethyl 1-methyl-2,8-dioxo-1,2,7,8-tetrahydropyrido[2,3-d]pyridazine-3-carboxylate which was used directly in the next step.

In a RBF equipped with reflux condenser, ethyl 1-methyl-2,8-dioxo-1,2,7,8-tetrahydropyrido[2,3-d]pyridazine-3-carboxylate (1.65 g, 6.63 mmol) was treated with phosphorus oxychloride (8.00 mL, 85.8 mmol). The reaction mixture was stirred in an oil bath at 110° C. for 90 min, and then cooled to RT. The volatiles were removed in vacuo and the residue was treated with $CH_2Cl_2$ then concentrated in vacuo. The residue was treated with $CH_2Cl_2/Et_2O$ and the resulting suspended solid was collected by suction filtration and dried in vacuo to give ethyl 8-chloro-1-methyl-2-oxo-1,2-dihydropyrido[3,2-d]pyridazine-3-carboxylate as a green solid. MS (ESI, pos. ion) m/z: 268 (M+1).
$^1$H NMR (400 MHz, CDCl$_3$) ppm 1.43 (t, J=7.0 Hz, 3H), 4.09 (s, 3H), 4.45 (q, J=7.0 Hz, 2H), 8.29 (s, 1H), 9.11 (s, 1H).

Step 7: 8-(2,4-Difluorophenyl)-1-methyl-2-oxo-1,2-dihydropyrido[3,2-d]pyridazine-3-carboxylic acid (7)

To a suspension of ethyl 8-chloro-1-methyl-2-oxo-1,2-dihydropyrido[3,2-d]pyridazine-3-carboxylate (6) (1.40 g, 5.23 mmol) in 3:1 1,4-dioxane: 2 M aq $Na_2CO_3$ (16 mL) was added 2,4-difluorophenylboronic acid (1.03 g, 6.54 mmol) and tetrakis(triphenylphosphine)palladium (0) (0.484 g, 0.418 mmol). The reaction mixture was heated in a microwave at 100° C. for 75 min, then more $Na_2CO_3$ solid (100 mg) was added and the reaction mixture was heated in the microwave at 100° C. for an additional 2 h. The mixture was diluted with water and washed with $CH_2Cl_2$. The aqueous layer was then acidified with 5 N HCl to pH ~2 and extracted with CHCl$_3$/iPrOH (4:1). The combined organic extracts were dried over MgSO$_4$, filtered, and concentrated in vacuo to give 8-(2,4-difluorophenyl)-1-methyl-2-oxo-1,2-dihydropyrido[3,2-d]pyridazine-3-carboxylic acid as a brown solid. MS (ESI, pos. ion) m/z: 318 (M+1).
$^1$H NMR (400 MHz, DMSO-$d_6$) ppm, 3.13 (s, 3H), 7.29-7.40 (m, 1H), 7.50 (td, J=2.4, 9.8 Hz, 1H), 7.82 (td, J=6.7, 8.6 Hz, 1H), 8.77 (s, 1H), 9.57 (s, 1H).

Step 8: 3-Bromo-8-(2,4-difluorophenyl)-1-methylpyrido[3,2-d]pyridazin-2(1H)-one (8)

To a suspension of 8-(2,4-difluorophenyl)-1-methyl-2-oxo-1,2-dihydropyrido[3,2-d]pyridazine-3-carboxylic acid (7) (1.00 g, 3.15 mmol) in 10:1 THF:H$_2$O (11 mL), stirred at 55° C., was added lithium acetate dihydrate (67 mg, 0.66 mmol). The mixture was stirred at 55° C. and treated with NBS (1.51 g, 8.48 mmol) in three equal portions at 30 min intervals. After addition of NBS was complete, the reaction mixture was stirred an additional 1 h at 55° C. In a separate flask, a suspension of 8-(2,4-difluorophenyl)-1-methyl-2-oxo-1,2-dihydropyrido[3,2-d]pyridazine-3-carboxylic acid (7) (0.92 g, 2.89 mmol) in 10:1 THF:H$_2$O (10 mL) stirred at 55° C. was treated with lithium acetate dihydrate (62 mg, 0.61 mmol) followed by NBS (1.39 g, 7.80 mmol) under the same conditions. Upon complete reaction, the two reaction mixtures were combined, diluted with water, and extracted with CH$_2$Cl$_2$. The combined organic layers were washed with 20% THF in water, dried over MgSO$_4$, filtered, and concentrated in vacuo. The resulting residue was purified by silica gel chromatography [eluting with a gradient of 10-40% B in A where the eluents were: A=CH$_2$Cl$_2$; B=1:49.5:49.5 MeOH:EtOAc:CH$_2$Cl$_2$] to give 3-bromo-8-(2,4-difluorophenyl)-1-methylpyrido[3,2-d]pyridazin-2(1H)-one as a yellow solid. MS (ESI, pos. ion) m/z: 350, 352 (M+1, M+3).
$^1$H NMR (400 MHz CDCl$_3$) ppm 3.36 (s, 3H), 6.92-7.04 (m, 1H), 7.15 (td, J=2.0, 8.2 Hz, 1H), 7.78 (td, J=6.3, 8.4 Hz, 1H), 8.26 (s, 1H), 9.17 (s, 1H).

Step 9: 8-(2,4-Difluorophenyl)-3-(2,4-difluorophenylamino)-1-methylpyrido[3,2-d]pyridazin-2(1H)-one (9)

To a suspension of 3-bromo-8-(2,4-difluorophenyl)-1-methylpyrido[3,2-d]pyridazin-2(1H)-one (8) (60.0 mg, 0.170 mmol) in toluene (2 mL) was added palladium (II) acetate (1.91 mg, 0.00852 mmol), 4,5-bis(diphenylphosphino)-9,9-dimethylxanthene (Xantphos) (9.86 mg, 0.0170 mmol) and cesium carbonate (83.3 mg, 0.256 mmol) followed by 2,4-difluorobenzenamine (0.0260 mL, 0.256 mmol). The reaction mixture was stirred and heated in a microwave at 110° C. for 75 min and then cooled to RT to afford a suspension. The solid was collected by suction filtration, washed with toluene and water, and dried in vacuo to give 8-(2,4-difluorophenyl)-3-(2,4-difluorophenylamino)-1-methylpyrido[3,2-d]pyridazin-2(1H)-one as a pale yellow solid. MS (ESI, pos. ion) m/z: 401 (M+1).

$^1$H NMR (400 MHz, DMSO-$d_6$) δ ppm 3.21 (s, 3H), 6.76 (d, J=2.5 Hz, 1H), 7.21 (t, J=8.5 Hz, 1H), 7.27-7.39 (m, 1H), 7.40-7.61 (m, 3H), 7.79 (td, J=6.7, 8.5 Hz, 1H), 8.66 (s, 1H), 9.25 (s, 1H).

EXAMPLE 2

Via Method A

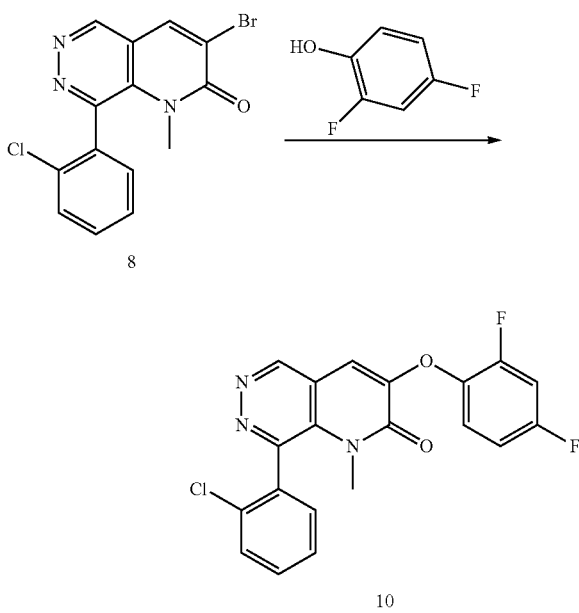

Synthesis of 8-(2-Chlorophenyl)-3-(2,4-difluorophenoxy)-1-methylpyrido[3,2-d]pyridazin-2(1H)-one (10)

Step 1: To a suspension of 3-bromo-8-(2-chlorophenyl)-1-methylpyrido[3,2-d]pyridazin-2(1H)-one (8) (90.0 mg, 0.26 mmol) in 2 mL of toluene was added 2,4-difluorophenol (30.6 μA 0.32 mmol), palladium diacetate (5.76 mg, 25.7 μmol), cesium carbonate (125 mg, 0.39 mmol) and 4,5-bis(diphenylphosphino)-9,9-dimethylxanthene (29.7 mg, 51.3 μmol). The reaction was heated in microwave at 120° C. for 1 h. The mixture was diluted with water, and extracted twice with $CHCl_3$/iPrOH (4:1). The combined organic layers were dried, filtered and concentrated. The residue was purified with RP-HPLC [using a gradient of 10-65% (0.1% TFA in acetonitrile) in (0.1% TFA in water)] and the fractions containing the compound were concentrated to remove MeCN and then treated with 2 M $Na_2CO_3$. It was extracted with EtOAc. The organic extract was dried and concentrated to give 8-(2-chlorophenyl)-3-(2,4-difluorophenoxy)-1-methylpyrido[3,2-d]pyridazin-2(1H)-one as a white solid. MS (ESI, pos. ion) m/z: 400 (M+1).

$^1$H NMR (400 MHz, DMSO-$d_6$) δ ppm 9.37 (1H, s), 7.72 (1H, dd, J=7.2, 1.8 Hz), 7.56-7.69 (4H, m), 7.47-7.56 (1H, m), 7.42 (1H, s), 7.20-7.29 (1H, m), 3.11 (3H, s).

These detailed descriptions of the Examples fall within the scope, and serve to exemplify the above-described General Synthetic Procedures which form part of the invention. These detailed descriptions are not intended as a restriction on the scope of the invention.

The following Examples in Table 1 will further assist in understanding and appreciating the invention. The compounds of examples 1-12 were made in accordance with exemplary method A, which corresponds to above described Example 1, respectively, and more generally to scheme 1. The compound examples were named according to the ACD naming convention, as associated with ISIS software. The mass spectral data is recorded M+H$^+$, which is the positive ion as measured by an electrospray ionization method. The biological assay data is provided for those exemplary compounds in Table 1 which were tested in, and data calculated from, the human whole blood and cellular assays. Not every compound example was run in the assays at the time of filing of this application, and accordingly no data is provided in the Table.

TABLE 1

| Ex. No | Name | MS (M+H+) | Method | WB TNF/IL8 IC50 (nM) | p38a IC50 (nM) |
|---|---|---|---|---|---|
| 1 | 8-(2,4-difluorophenyl)-3-(2,4-difluorophenylamino)-1-methylpyrido[3,2-d]pyridazin-2(1H)-one | 401 | A | 14 | 0.8 |
| 2 | 8-(2,4-difluorophenyl)-3-(4-fluorophenoxy)-1-methylpyrido[3,2-d]pyridazin-2(1H)-one | 384 | A | 273 | 102 |
| 3 | 3-(2,4-difluorophenylamino)-8-(2-fluoro-4-(trifluoromethyl)phenyl)-1-methylpyrido[3,2-d]pyridazin-2(1H)-one | 451 | A | 147 | 2.3 |

TABLE 1-continued

| Ex. No | Name | MS (M+H+) | Method | WB TNF/IL8 IC50 (nM) | p38a IC50 (nM) |
|---|---|---|---|---|---|
| 4 | 8-(2,4-difluorophenyl)-3-((5-fluoro-2-pyridinyl)amino)-1-methylpyrido[2,3-d]pyridazin-2(1H)-one | 384 | A | >2500 | 327 |
| 5 | 8-(2,4-difluorophenyl)-3-((2,4-difluorophenyl)amino)-1-ethylpyrido[2,3-d]pyridazin-2(1H)-one | 415 | A | 3 | 0.2 |
| 6 | 8-(2-chlorophenyl)-3-(2,4-difluorophenoxy)-1-methylpyrido[2,3-d]pyridazin-2(1H)-one | 400 | A | 7.8 | 0.6 |
| 7 | 8-(2,4-difluorophenyl)-3-((3,5-difluoro-2-pyridinyl)amino)-1-methylpyrido[2,3-d]pyridazin-2(1H)-one | 402 | A | >2500 | 111 |
| 8 | 3-((2,4-difluorophenyl)amino)-1-methyl-8-(2-methyl-4-(methylsulfonyl)phenyl)pyrido[2,3-d]pyridazin-2(1H)-one | 457 | A | 13 | 1.7 |
| 9 | 3-(2,4-difluorophenoxy)-1-methyl-8-(2-methyl-4-(methylsulfonyl)phenyl)pyrido[2,3-d]pyridazin-2(1H)-one | 458 | A | 110 | 11 |
| 10 | 8-(2-chloro-4-(methylsulfonyl)phenyl)-3-((2,4-difluorophenyl)amino)-1-methylpyrido[2,3-d]pyridazin-2(1H)-one | 477 | A | 10 | 0.8 |
| 11 | 8-(2,4-difluorophenyl)-3-((4-fluorophenyl)amino)-1-methylpyrido[2,3-d]pyridazin-2(1H)-one | 383 | A | 54 | 2.2 |
| 12 | 3-(2,4-difluorophenoxy)-8-(2,4-difluorophenyl)-1-methylpyrido[2,3-d]pyridazin-2(1H)-one | 402 | A | 42 | 8.4 |

The following Examples in Table 2 are additional representative compounds which will further assist in understanding and appreciating the invention. The compounds are named according to the ACD naming convention, as associated with ISIS software.

TABLE 2

| Ex. No. | Compound Name | Chemical Structure |
|---|---|---|
| 13 | 8-(2,4-difluorophenyl)-1-methyl-3-(pyridin-4-ylamino)pyrido[2,3-d]pyridazin-2(1H)-one | 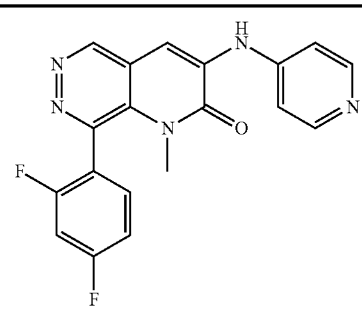 |
| 14 | 3-(cyclohexylamino)-8-(2,4-difluorophenyl)-1-methylpyrido[2,3-d]pyridazin-2(1H)-one | 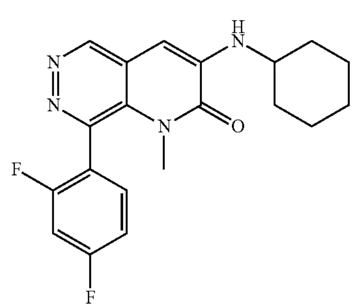 [SMILES: Cn1c(=O)c(NC2CCCCC2)cc2cnnc(-c3ccc(F)cc3F)c21] |

TABLE 2-continued

| Ex. No. | Compound Name | Chemical Structure |
|---|---|---|
| 15 | 8-(2,4-difluorophenyl)-3-((4-fluorophenyl)(methyl)amino)-1-methylpyrido[2,3-d]pyridazin-2(1H)-one | 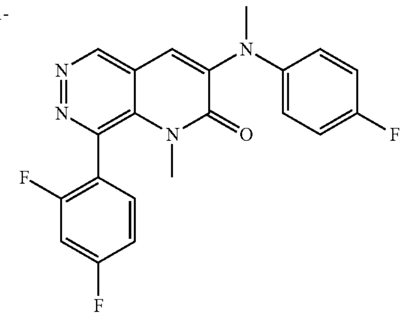 |
| 16 | 8-(2,4-difluorophenyl)-1-methyl-3-(phenylthio)pyrido[2,3-d]pyridazin-2(1H)-one | 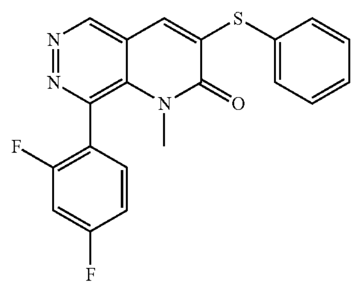 [SMILES: Cn1c(=O)c(Sc2ccccc2)cc2cnnc(-c3ccc(F)cc3F)c21] |
| 17 | 3-(cyclohexyloxy)-8-(2,4-difluorophenyl)-1-methylpyrido[2,3-d]pyridazin-2(1H)-one | 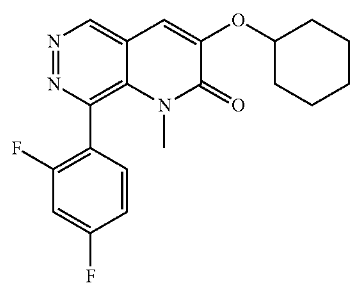 [SMILES: Cn1c(=O)c(OC2CCCCC2)cc2cnnc(-c3ccc(F)cc3F)c21] |
| 18 | 8-(2-chlorophenyl)-1-methyl-3-(pyridin-4-yloxy)pyrido[2,3-d]pyridazin-2(1H)-one | 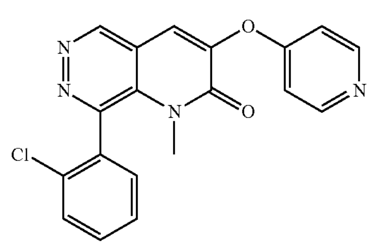 [SMILES: Cn1c(=O)c(Oc2ccncc2)cc2cnnc(-c3ccccc3Cl)c21] |
| 19 | 3-(4-fluorophenylamino)-1-methyl-8-(4-methylpyridin-3-yl)pyrido[2,3-d]pyridazin-2(1H)-one | 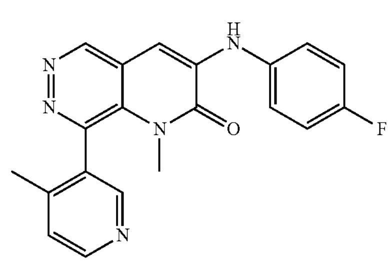 [SMILES: Cc1ccncc1-c1nncc2cc(Nc3ccc(F)cc3)c(=O)n(C)c12] |

TABLE 2-continued

| Ex. No. | Compound Name | Chemical Structure |
|---|---|---|
| 20 | 3-(4-fluorophenoxy)-1-methyl-8-morpholinopyrido[2,3-d]pyridazin-2(1H)-one | 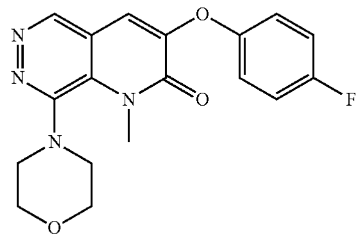 [SMILES: Cn1c(=O)c(Oc2ccc(F)cc2)cc2cnnc(N3CCOCC3)c21] |
| 21 | 8-cyclohexyl-3-(2,4-difluorophenylamino)-1-methylpyrido[2,3-d]pyridazin-2(1H)-one | 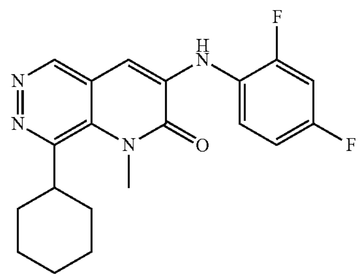 [SMILES: Cn1c(=O)c(Nc2ccc(F)cc2F)cc2cnnc(C3CCCCC3)c21] |
| 22 | 8-(cyclohexyloxy)-3-(4-fluorophenylamino)-1-methylpyrido[2,3-d]pyridazin-2(1H)-one | 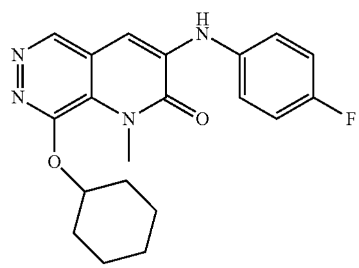 [SMILES: Cn1c(=O)c(Nc2ccc(F)cc2)cc2cnnc(OC3CCCCC3)c21] |
| 23 | 3-(cyclohexylamino)-8-(1,3-dimethyl-1H-pyrazol-4-yl)-1-methylpyrido[2,3-d]pyridazin-2(1H)-one | 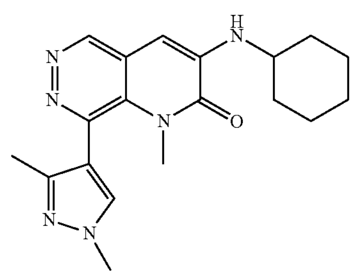 [SMILES: Cc1nn(C)cc1-c1nncc2cc(NC3CCCCC3)c(=O)n(C)c12] |

The following compounds in Table 3 are additional representative examples of Formula I as provided by the present invention.

TABLE 3

| Ex. No. | $R^1$ | $R^4$ | X | W | $R^5$ |
|---|---|---|---|---|---|
| 24 | 3,5-difluoro-Ph | —CH$_2$CH$_3$ | O | —NH— | oxazolyl |
| 25 | morpholine | —CH$_3$ | O | —O— | 3,5-difluoro-Ph |
| 26 | piperazine | —CH$_2$CH$_3$ | S | —NH— | 2,4-difluoro-Ph |
| 27 | piperidine | —CH$_3$ | S | —O— | 2,6-difluoro-Ph |
| 28 | phenyl | —CH$_3$ | O | —S— | 3-Cl, 5-F—Ph |
| 29 | m-CH$_3$-phenyl- | —CH$_2$CH$_3$ | O | —NH— | 3,5-diCH$_3$—Ph |
| 30 | m-Cl-phenyl- | —CH$_2$CH$_3$ | O | —NH— | 3,5-difluoro-Ph |
| 31 | o-CH$_3$-phenyl- | —CH$_2$CH$_3$ | O | —NH— | pyridyl |
| 32 | —S-Phenyl | —CH$_3$ | S | —O— | morpholinyl |
| 33 | —NH-phenyl | —OCH$_3$ | S | —O— | 4-F—Ph |

TABLE 3-continued

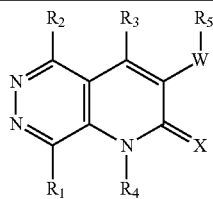

| Ex. No. | $R^1$ | $R^4$ | X | W | $R^5$ |
|---|---|---|---|---|---|
| 34 | —O-isopropyl | —CH$_2$CH$_3$ | O | —NH— | 3-F—Ph |
| 35 | morpholine | —CH$_3$ | O | —NH— | 2-F—Ph |
| 36 | N—CH$_3$-imidazole | —OCH$_3$ | O | —S— | imidazolyl |
| 37 | pyrazole | —CH$_2$CH$_3$ | O | —O— | pyrazolyl |
| 38 | triazole | —CH$_3$ | S | —O— | furanyl |
| 39 | thiophene | —OCH$_3$ | S | —NH— | thiadiazolyl |
| 40 | 2-CH$_3$-thiophene | —CH$_2$CH$_3$ | O | —O— | isothiazolyl |
| 41 | —NH-cyclohexyl | —CH$_2$CH$_3$ | O | —S— | cyclopropyl |
| 42 | —NH-cyclopropyl | —CH$_3$ | O | —O— | 4-F—Ph |
| 43 | —O-isobutyl | —OCH$_3$ | O | —S— | Cyclopentyl |
| 44 | 2,4-difluoro-Ph | —CH$_2$CH$_3$ | S | —NH— | isothiazolyl |
| 45 | 2,6-difluoro-Ph | —CH$_3$ | S | —NH— | cyclohexyl |
| 46 | 2,6-difluoro-Ph | —CH$_3$ | O | —O— | 4-F—Ph |
| 47 | o-CH$_3$-phenyl | —OCH$_3$ | O | —NH— | 3-pyridyl |
| 48 | —S-Phenyl | —CH$_2$CH$_3$ | O | —NHCH$_3$— | imidazolyl |
| 49 | —NH-phenyl | —CH$_3$ | O | —O— | pyrazolyl |
| 50 | —O-isopropyl | —OCH$_3$ | S | —S— | furanyl |
| 51 | morpholine | —CH$_2$CH$_3$ | S | —S— | thiadiazolyl |

While the examples and schemes described above provide processes for synthesizing compounds, and intermediates thereof, of Formulas I, I-B, I-C and I-D, it should be appreciated that other methods may be utilized to prepare such compounds. Methods involving the use of protecting groups may be used. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protecting groups may already be present in precursors and should protect the functional groups concerned against unwanted secondary reactions, such as acylations, etherifications, esterifications, oxidations, solvolysis, and similar reactions. It is a characteristic of protecting groups that they readily lend themselves, i.e. without undesired secondary reactions, to removal, typically accomplished by solvolysis, reduction, photolysis or other methods of removal such as by enzyme activity, under conditions analogous to physiological conditions. It should also be appreciated that the protecting groups should not be present in the end-products. Persons of ordinary skill in the art know, or can easily establish, which protecting groups are suitable with the reactions described herein.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981), in Methoden der Organischen Chemie (Methods of Organic Chemistry), Houben Weyl, 4$^{th}$ edition, Volume 15/1, Georg Thieme Verlag, Stuttgart (1974), in H.-D. Jakubke and H. Jescheit, Aminosäuren, Peptide, Proteine (Amino Acids, Peptides, Proteins), Verlag Chemie, Weinheim, Deerfield Beach, and Basel (1982), and in Jochen Lehmann, Chemie der Kohlenhydrate: Monosaccharide and Derivate (Chemistry of Carbohydrates: Monosaccharides and Derivatives), Georg Thieme Verlag, Stuttgart (1974).

Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary salt forms and their preparation are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H$^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., ethyl acetate; ethers including aliphatic ethers, e.g., Et$_2$O and ethylene glycol dimethyl ether or cyclic ethers, e.g., THF; liquid aromatic hydrocarbons, including benzene, toluene and xylene; alcohols, including MeOH, EtOH, 1-propanol, IPOH, n- and t-butanol; nitriles including CH$_3$CN; halogenated hydrocarbons, including CH$_2$Cl$_2$, CHCl$_3$ and CCl$_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, H$_2$SO$_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise provided by this invention. Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

In synthesizing a compound of formulas I, I-B, I-C and I-D according to a desired procedure, the steps may be performed in an order suitable to prepare the compound, including a procedure described herein or by an alternate order of steps described herein, and may be preceded, or followed, by additional protection/deprotection steps as necessary. The procedures may further use appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2nd edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

In one embodiment, the present invention provides a method of making a compound of Formula I-B, the method comprising the step of reacting a compound 7

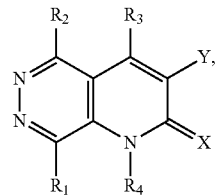

wherein $R^1$, $R^2$, $R^3$, $R^4$ and X are as defined herein and Y is a halogen, with a nucleophilic compound W having a general formula

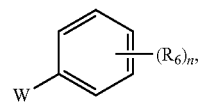

wherein W and $R^6$ are as defined herein and n is 0, 1, 2, 3, 4 or 5, to make a compound of Formula I-B.

In another embodiment, the present invention provides a method of making a compound of Formula I-A, the method comprising the step of reacting a compound 7

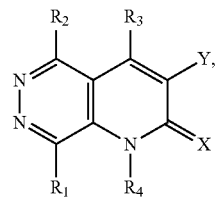

wherein $R^1$, $R^2$, $R^3$, $R^4$ and X are as defined herein and Y is a halogen, with a boronic acid having a general formula $NH_2$—$R^5$, wherein $R^5$ is as defined herein, to make a compound of Formula I-A.

In another embodiment, the present invention provides a method of making a compound of Formula I-A, the method comprising the step of reacting a compound 7

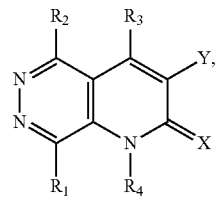

wherein $R^1$, $R^2$, $R^3$, $R^4$ and X are as defined herein and Y is a halogen, with a boronic acid having a general formula HO—$R^5$, wherein $R^5$ is as defined herein, to make a compound of Formula I-A.

Compounds of the present invention can possess, in general, one or more asymmetric carbon atoms and are thus capable of existing in the form of optical isomers including, without limitation, racemates and racemic mixtures, scalemic mixtures, single enantiomers, individual diastereomers and diastereomeric mixtures. All such isomeric forms of these compounds are expressly included in the present invention. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may also be represented in multiple tautomeric forms. The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

Biological Evaluation

The compounds of the invention may be modified by appending appropriate functionalities to enhance selective biological properties. Such modifications are known in the art and include those which increase biological penetration into a given biological compartment (e.g., blood, lymphatic system, central nervous system), increase oral bioavailability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

Although the pharmacological properties of the compounds of the invention (Formulas I, I-B and I-C, and I-D) vary with structural change, in general, activity possessed by compounds of Formulas I and II may be demonstrated both in vitro as well as in vivo. Particularly, the pharmacological properties of the compounds of this invention may be confirmed by a number of pharmacological in vitro assays, as well as in-vivo animal models.

The following assays were used to characterize the ability of compounds of the invention to modulate the activity of human p38 enzyme, inhibit the production of TNF-α and interleukin cytokines, including IL-1, IL-1β, IL-6 and IL-8 and/or evaluate efficacy of a compound in an in vivo animal model. Another assay, a cyclooxygenase enzyme (COX-1 and COX-2) inhibition activity in vitro assay, can be used to characterize the ability of compounds of the invention to inhibit COX-1 and/or COX-2.

Purified and Activated Recombinant Human p38α Assay

Kinase Reaction Buffer: Kinase reaction buffer for p38α HTRF assays consists of 50 mM Tris-pH 7.5, 5 mM MgCl$_2$, 0.1 mg/mL BSA, 100 μM Na$_3$VO$_4$ and 0.5 mM DTT.

HTRF Detection Buffer: HTRF detection buffer contains 100 mM HEPES-pH 7.5, 100 mM NaCl, 0.1% BSA, 0.05% Tween-20, and 10 mM EDTA.

Serial Dilution of Compounds: Compounds were dissolved in 100% DMSO and serially diluted (3 fold, 10 point) in a polypropylene 96-well microtiter plate (drug plate). The final starting concentration of compounds in the p38α enzymatic assays was 1 μM. Columns 6 and 12 (HI controls and LO controls respectively) in the drug plate were reserved as controls and contained only DMSO.

Kinase Reaction: The p38α kinase reactions were carried out in a polypropylene 96-well black round bottom assay plate in total volume of 30 μL kinase reaction buffer. Appropriate concentration of purified and activated enzyme (recombinant human) was mixed with indicated concentration of ATP and 100 nM GST-ATF2-Avitag, in the presence or absence (HI control) of Compound. See table below for actual concentrations. In the absence of substrate, the background was measured as LO control. The reaction was allowed to incubate for 1 hour at RT.

Assay Reagent Concentrations: The final reagent concentrations were 1 nM p38α and 50 μM ATP. The Km for ATP of the enzyme was 103 μM, giving a ratio of ATP concentration to Km of 0.49.

HTRF Detection: The kinase reaction was terminated and phospho-ATF2 was revealed by addition of 30 μL of HTRF detection buffer supplemented with 0.1 nM Eu-anti-pTP and 4 nM SA-APC. After 60 minutes incubation at room temperature, the assay plate was read in a Discovery Plate Reader. The wells were excited with coherent 320 nm light and the ratio of delayed (50 ms post excitation) emissions at 620 nM (native europium fluorescence) and 665 nm (europium fluorescence transferred to allophycocyanin—an index of substrate phosphorylation) was determined (Park et al, 1999).

Data Analysis: The proportion of substrate phosphorylated in the kinase reaction in the presence of compound compared with that phosphorylated in the presence of DMSO vehicle alone (HI control) was calculated using the formula: % control (POC)=(compound−average LO)/(average HI−average LO)*100. Data (consisting of POC and inhibitor concentration in μM) was fitted to a 4-parameter equation (y=A+((B−A)/(1+((x/C)^D))), where A is the minimum y (POC) value, B is the maximum y (POC), C is the x (compound concentration) at the point of inflection and D is the slope factor, using a Levenburg-Marquardt non-linear regression algorithm.

The inhibition constant (Ki) of the inhibitor was estimated from the $IC_{50}$ (compound concentration at the point of inflection C) using the Cheng-Prussof equation: $Ki=IC_{50}/(1+S/Km)$, where S is the ATP substrate concentration, and Km is the Michaelis constant for ATP as determined experimentally. All results were expressed as the mean±the standard error of the mean. Data acquisition and non-linear regression algorithms were performed using Activity Base v5.2 and XL-fit software v4.1 respectively. All data was archived using Activity Base v5.2 software. Data for Exemplary compounds in the human p38-alpha enzyme assay is provided in Table 1. Examples 1-3 and 5-12 exhibited $IC_{50}$ values of less than or equal to 125 nM.

Lipopolysaccharide-Activated PBMC Cytokine Production Assay

Isolation of PBMC

Test compounds were evaluated in vitro for the ability to inhibit the production of IL-1β, IL-6, and TNF-α by PBMC activated with bacterial lipopolysaccharide (LPS). Fresh leukocytes were obtained from a local blood bank, and peripheral blood mononuclear cells (PBMCs) were isolated by density gradient centrifugation on Ficol-Paque Plus (Pharmacia).

Preparation of Test Compound Stock Solutions

All reagents were prepared in RPMI 1640+10% v/v human AB serum+1× Pens/Strep/Glu (assay medium). Test compounds were dissolved in 100% DMSO and serially diluted in 96-well polypropylene round bottom micro titer plates (drug plate). Serial dilutions were then diluted 1:250 into assay medium to a 4× working concentration. Compound serial dilutions were half-log, 10 point titrations with a final starting concentration of 1 μM.

Treatment of Cells with Test Compounds and Activation with Lipopolysaccharide

LPS was prepared to a 4× concentration in assay medium. 100 μl of PBMC (1×10^6 cells/ml) were plated in a 96-well polystyrene flat bottom micro titer tissue culture plate and incubated with 50 μl of 4× compound serial dilution for 1 hour at 37° C., 5% $CO_2$ in a tissue culture incubator. 50 μl 4×LPS or control was added and the plates were incubated at 37° C., 5% $CO_2$ in a tissue culture incubator for 18 hours. The final DMSO concentration was 0.1%. The total volume was 200 μL. The final LPS concentration was 100 ng/mL. After 18 hours culture supernatants were removed and IL-1β, IL-6, and TNF-α presence in the supernatants was quantified using MSD ECL based technology.

Cytokine Measurements

20 μL of culture supernatant were added to MSD plates, and incubated for one hour at room temperature. 20 μL of detection antibody diluted in antibody diluent (1 μg/mL), and 110 μL of 2× Read Buffer P was added, and incubated for one hour at RT. Electrochemiluminescence was measured using the SECTOR HTS Imager (MSD, Gaithersburg, Md.).

Data Analysis

Compound $IC_{50}$ values were calculated as follows: The proportion of cytokine production in the presence of compound compared to the cytokine production in the presence of the DMSO vehicle alone (Hi control) was calculated using the formula: Percent Control (POC)=(compound−average Lo)/(average Hi−average Lo)*100. To derive $IC_{50}$ values, POC was plotted against the Log of compound concentration (μM) and fitted to a 4-parameter equation (y=A+((B−A)/(1+((x/C)^D))), where A is the minimum y (POC) value, B is the maximum y (POC), C is the concentration of compound at the inflection point, and D is the slope factor, using a Levenburg-Marquardt non-linear regression algorithm. Data acquisition and non-linear regression were performed using Activity Base and XL-fit respectively. The compounds of Examples 1-3,5,6, and 8-12 exhibited activities in the whole blood PMBC assay with $IC_{50}$ values of equal to 1000 nM or less.

Compounds of the invention can also be shown to inhibit LPS-induced release of IL-1β, IL-6 and/or IL-8 from PBMC by measuring concentrations of IL-1β, IL-6 and/or IL-8 by methods well known to those skilled in the art. In a similar manner to the above described assay involving the LPS induced release of TNF-α from PBMC, compounds of this invention can also be shown to inhibit LPS induced release of IL-1β, IL-6 and/or IL-8 from PBMC by measuring concentrations of IL-1β, IL-6 and/or IL-8 by methods well known to those skilled in the art. Thus, the compounds of the invention may lower elevated levels of TNF-α, IL-1, IL-6, and IL-8 levels. Reducing elevated levels of these inflammatory cytokines to basal levels or below is favorable in controlling, slowing progression, and alleviating many disease states. All of the compounds are useful in the methods of treating disease states in which TNF-α, IL-1β, IL-6, and IL-8 play a role to the full extent of the definition of TNF-α-mediated diseases described herein.

Lipopolysaccharide-activated THP1 Cell TNF Production Assay

THP1 cells were resuspended in fresh THP1 media (RPMI 1640, 10% heat-inactivated FBS, 1×PGS, 1×NEAA, plus 30 μM βME) at a concentration of 1.5×10^6 cells per mL. One hundred microliters of cells per well were plated in a polystyrene 96-well tissue culture plate. 1.5 micrograms per mL of bacterial LPS was prepared in THP1 media and transferred to the first 11 columns of a 96-well polypropylene plate. Column 12 contained only THP1 media for the LO control. Compounds were dissolved in 100% DMSO and serially diluted 3 fold in a polypropylene 96-well microtiter plate (drug plate). Columns 6 and 12 were reserved as controls (HI controls and LO controls respectively) and contained only DMSO. 10 μL of LPS followed by one microliter of inhibitor compound from the drug plate was transferred to the cell plate. The treated cells were induced to synthesize and secrete TNF-α in a 37° C. humidified incubator with 5% $CO_2$ for 3 hours. Fifty microliters of conditioned media was transferred to a 96-well MULTI-ARRAY™ 96-well small spot plate—custom coated with MAB610 containing 100 μL of 2× Read Buffer P supplemented with 0.34 nM AF210NA polyclonal Ab labeled with ruthenium (MSD-Sulfo-TAG™—NHS ester). After an overnight incubation at room temperature with shaking, the reaction was read on the Sector Imager™ 6000. A low voltage was applied to the ruthenylated TNF-α immune complexes, which in the presence of TPA (the active component in the ECL reaction buffer, Read Buffer P), resulted in a cyclical redox reaction generating light at 620 nm. The amount of secreted TNF-α in the presence of test compounds compared with that in the presence of DMSO vehicle alone (HI control) was calculated using the formula: % control (POC)=(cpd−average LO)/(average HI−averageLO)*100. Data (consisting of POC and inhibitor concentration in μM) was fitted to a 4-parameter equation (y=A+((B−A)/(1+((x/C)^D))), where A is the minimum y (POC) value, B is the maximum y (POC), C is the x (cpd concentration) at the point of inflection and D is the slope factor) using a Levenburg-Marquardt non-linear regression algorithm. The compounds of Examples 1-2 exhibited activities in the THP-1 cellular TNF production assay with $IC_{50}$ values of 1000 nM or less.

Inhibition of TNF-α Induced IL-8 in 50% Human Whole Blood

Test compounds were evaluated in vitro for the ability to inhibit the production of secreted IL-8 by whole blood activated with TNF-α. Fresh human whole blood was obtained from healthy, non-medicated volunteers in sodium heparin tubes.

Compound Dilution—Assay Procedure

Test compounds are serially diluted 1:3 in DMSO and then diluted 1:250 into R10 (RPMI 1640, 10% human serum AB, 1× pen/strep/glutamine) to the 4× working concentration to be used in the assay. 100 ul heparinized whole blood is plated into wells of 96 well flat bottom plates. 50 ul of either 4× compound or DMSO control (Final DMSO concentration is 0.1%) are added to the appropriate wells. Plates are incubated for 1 hour at 37 degrees Celsius. 50 ul of 4×TNF-α (4 nM TNF-α, for a final concentration of 1 nM) or control (media alone) is added to the appropriate wells (Total volume=200 ul). Plates are incubated overnight (16-18 hours). 100 ul of supernatant is collected and stored in 96-well round bottom polypropylene plates at −80 degrees Celsius or assayed immediately for IL-8.

Cytokine Measurement

Cytokines are measured on antibody (Ab) sandwich ECL based 96-well detection plates. 20 ul of supernatant are added to plate and plate is sealed and shaken at RT for 1 hour. 130 ul of detection Ab cocktail is added and plates are sealed and shaken for 1 hour in the dark at RT. Plates are read on MSD Sector HTS instrument. Data are analyzed and $IC_{50}$ values generated using Activity Base and X1-fit programs. Data for exemplary compounds in the TNF-α Induced IL-8 in 50% Human Whole Blood assay is provided in Tables 1. Examples 1-3,5,6, and 8-12 exhibited $IC_{50}$ values of less than or equal to 300 nM.

Inhibition of LPS-Induced TNF-α Production Rats

LPS was diluted in PBS (100 μg per rat). Rats (n=6) were pretreated with vehicle or compound (0.03, 0.1, 0.3 and 1.0 mg/kg, PO) 60 minutes prior to the injection of LPS (100 μg per rat/IV, tail vein). Blood was harvested via decapitation 90 minutes following the administration of LPS. Blood was centrifuged at 12,000 rpm for 12 minutes to obtain plasma. Plasma samples were stored at −80 C. TNF-α levels were determined by ELISA for treatment groups that received LPS. Rat TNF-α levels were analyzed using rat TNF-α CytoSet kit from Biosource International. ELISA was completed according to the manufacturer's instructions. The concentration of TNF-α was interpolated from absorbance using the standard curve generated. For each individual sample, the TNF value from the dilution series that fell in the most linear portion of the standard curve was chosen and used for data analysis. The limit of quantitation of the ELISA was 1,000 pg/mL.

Compounds of the invention may be shown to have anti-inflammatory properties in animal models of inflammation, including carageenan paw edema, collagen induced arthritis and adjuvant arthritis, such as the carageenan paw edema model (C. A. Winter et al., Proc. Soc. Exp. Biol. Med., 111: 544 (1962); K. F. Swingle, in R. A. Scherrer and M. W. Whitehouse, Eds., Anti-inflammatory Agents, Chemistry and Pharmacology, 13(II):33, Academic, New York (1974) and collagen induced arthritis (D. E. Trentham et al., J. Exp. Med., 146:857 (1977); J. S. Courtenay, Nature (New Biol.), 283:666 (1980)).

Collagen-induced Arthritis (CIA) Model in Rats

Porcine type II collagen (10 mg) was dissolved in 0.1N acetic acid (5 mL) two days prior to use on a rotating plate in the refrigerator. Subsequently, collagen was emulsified 1:1 with Freund's incomplete adjuvant using an emulsification needle and glass syringes yielding a final concentration of 1 mg/mL.

Disease was induced in each animal by intradermal injection of emulsified collagen in IFA at 10 different sites (100 μL per site) over the back. The clinical onset of arthritis varied between days 10 to 12 as indicated by hind paw swelling and ambulatory difficulties. At onset (defined as Day 0), rats were randomized to treatment groups and therapy was initiated with drug or vehicle control as noted in table above. Rats were treated for 7 days and were sacrificed on Day 8. Paw swelling and other measurements of efficacy is described Schett et al (Schett et al. Arthritis and Rheum. 52:1604 (2005). The compound examples may be shown to exhibit potency in the rat CIA model.

Cyclooxygenase Enzyme Activity Assay

The human monocytic leukemia cell line, THP-1, differentiated by exposure to phorbol esters expresses only COX-1; the human osteosarcoma cell line 143B expresses predominantly COX-2. THP-1 cells are routinely cultured in RPMI complete media supplemented with 10% FBS and human osteosarcoma cells (HOSC) are cultured in minimal essential media supplemented with 10% fetal bovine serum (MEM-10% FBS); all cell incubations are at 37° C. in a humidified environment containing 5% $CO_2$.

COX-1 Assay

In preparation for the COX-1 assay, THP-1 cells are grown to confluency, split 1:3 into RPMI containing 2% FBS and 10 mM phorbol 12-myristate 13-acetate (TPA), and incubated for 48 h on a shaker to prevent attachment. Cells are pelleted and resuspended in Hank's Buffered Saline (HBS) at a concentration of $2.5 \times 10^6$ cells/mL and plated in 96-well culture plates at a density of $5 \times 10^5$ cells/mL. Test compounds are diluted in HBS and added to the desired final concentration and the cells are incubated for an additional 4 hours. Arachidonic acid is added to a final concentration of 30 mM, the cells incubated for 20 minutes at 37° C., and enzyme activity determined as described below.

COX-2 Assay

For the COX-2 assay, subconfluent HOSC are trypsinized and resuspended at $3 \times 10^6$ cells/mL in MEM-FBS containing 1 ng human IL-1b/mL, plated in 96-well tissue culture plates at a density of $3 \times 10^4$ cells per well, incubated on a shaker for 1 hour to evenly distribute cells, followed by an additional 2 hour static incubation to allow attachment. The media is then replaced with MEM containing 2% FBS (MEM-2% FBS) and 1 ng human IL-1b/mL, and the cells incubated for 18-22 h. Following replacement of media with 190 mL MEM, 10 mL of test compound diluted in HBS is added to achieve the desired concentration and the cells incubated for 4 h. The supernatants are removed and replaced with MEM containing 30 mM arachidonic acid, the cells incubated for 20 minutes at 37° C., and enzyme activity determined as described below.

COX Activity Determined

After incubation with arachidonic acid, the reactions are stopped by the addition of 1N HCl, followed by neutralization with 1 N NaOH and centrifugation to pellet cell debris. Cyclooxygenase enzyme activity in both HOSC and THP-1 cell supernatants is determined by measuring the concentration of $PGE_2$ using a commercially available ELISA (Neogen #404110). A standard curve of $PGE_2$ is used for calibration, and commercially available COX-1 and COX-2 inhibitors are included as standard controls. Various compounds of the invention may be shown to inhibit the COX-1 and/or COX-2 activity.

Indications

Accordingly, compounds of the invention are useful for, but not limited to, the prevention or treatment of inflammation, pro-inflammatory cytokines levels including, without limitation, TNF, IL-1, IL-2, IL-6 and/or IL-8, and disease associated therewith. The compounds of the invention have p38 kinase modulatory activity. In one embodiment of the invention, there is provided a method of treating a disorder related to the activity of p38 enzyme in a subject, the method comprising administering to the subject an effective dosage amount of a compound of a compound of Formulas I, I-B or I-C, or I-D.

Accordingly, the compounds of the invention would be useful in therapy as anti-inflammatory agents in treating inflammation, or to minimize deleterious effects of p38. Based on the ability to modulate pro-inflammatory cytokine production, the compounds of the invention are also useful in treatment and therapy of cytokine-mediated diseases. Particularly, these compounds can be used for the treatment of rheumatoid arthritis, Pagets disease, osteoporosis, multiple myeloma, uveitis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses or herpes zoster infection, or any combination thereof, in a subject.

An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further applicable to the treatment of inflammation, e.g. inflammatory disease or condition, of connective tissues including dermatomyositis and myositis.

The compounds of the invention can also be used as active agents against such disease states as arthritis, atherosclerosis, psoriasis, psoriatic pain, atopic dermatitis hemoangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration.

The compounds of the invention are also useful in the treatment of diabetic conditions such as diabetic retinopathy and microangiopathy.

The compounds of the present invention are also useful for treating ankylosing spondylitis, inflammatory bowel disease, inflammatory pain, ulcerative colitis, Crohn's disease, asthma, chronic obstructive pulmonary disease, myelodysplastic syndrome, endotoxic shock, chronic hepatitis C or a combination thereof.

Thus, the present invention provides methods for the treatment of p38 protein kinase-associated disorders, comprising the step of administering to a subject, including human subjects, prophylactically or therapeutically, at least one compound of the Formula I or of Formula II in an amount effective therefore. Other therapeutic agents such as those described below may be employed with the inventive compounds in the present methods. In the methods of the present invention, such other therapeutic agent(s) may be administered prior to, simultaneously with or following the administration of the compound(s) of the present invention. The present invention also provides for a method for treating atopic dermatitis by administration of a therapeutically effective amount of a compound of the present invention to a patient, whether or not in need of such treatment.

In yet another embodiment, the compounds are useful for decreasing the level of, or lowering plasma concentrations of one or more of TNF-α, IL-1β, IL-6 and IL-8 in a subject, including human subjects, generally a mammal and typically a human.

In yet another embodiment, the compounds are useful for treating a pain disorder, such as inflammatory pain, psoriatic pain, arthritic pain and the like in a subject, including human subjects, by administering to the subject an effective dosage amount of a compound according to formulas I, I-B or I-C or I-D.

In yet another embodiment, the compounds are useful for treating diabetes in a subject, including human subjects, by administering to the subject an effective dosage amount of a compound according to formulas I, I-B or I-C or I-D, to produce a glucagon antagonist effect.

In yet another embodiment, the compounds are useful for decreasing prostaglandin production in a subject, including human subjects, by administering to the subject an effective dosage amount of a compound according to formulas I, I-B or I-C or I-D.

In yet another embodiment, the compounds are useful for decreasing cyclooxygenase enzyme activity in a subject, including human subjects, by administering to the subject an effective amount of a compound according to formulas I, I-B or I-C or I-D.

In yet another embodiment, the cyclooxygenase enzyme is COX-2.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating TNF-$\alpha$, IL-1, IL-6, and IL-8 mediated diseases, cancer, and/or hyperglycemia with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.001 mg/kg to 500 mg/kg, advantageously between about 0.005 and about 50 mg/kg, more advantageously about 0.005 and about 30 mg/kg, even more advantageously between about 0.005 and about 10 mg/kg, and even more advantageously about 0.01 and about 5 mg/kg, and should be useful for all methods of use disclosed herein. The daily dose can be administered in one to four doses per day.

While it may be possible to administer a compound alone, the compound of Formulas I, I-B or I-C or I-D is normally administered as an active pharmaceutical ingredient (API) in a composition comprising other suitable and pharmaceutically acceptable excipients. This admixture is typically referred to as a pharmaceutical composition. This composition should be pharmaceutically acceptable. In another embodiment, the invention provides a pharmaceutical composition comprising a compound of the present invention in combination with a pharmaceutically acceptable excipient. Pharmaceutical excipients generally include diluents, carriers, adjuvants and the like (collectively referred to herein as "excipient" materials) as described herein, and, if desired, other active ingredients. A pharmaceutical composition of the invention may comprise an effective amount of a compound of the invention or an effective dosage amount of a compound of the invention. An effective amount of the compound is typically that amount capable of bring about a desired physiological effect in the subject. An effective dosage amount of a compound of the invention may constitute administering to the subject one or more than one individual dosage units of the pharmaceutically acceptable composition comprising said compound. For example, where two or more unit dosages of a pharmaceutical composition, such as a tablet, pill, capsule, liquid, suspension and the like, may be required to administer an effective amount of the compound, then the effective dosage amount of the API is less than the effective amount of the API. Thus, an effective dosage amount may include an amount less than, equal to or greater than an effective amount of the compound. A suitable pharmaceutically acceptable composition, such as a powder, a liquid and the like, may exist in which the effective amount of the compound is administered by administering a portion of the composition and requiring the subject to take multiple doses over a specified period of time.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of API from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the compounds of this invention are ordinarily combined with one or more adjuvants or "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

In the case of psoriasis and other skin conditions, it may be preferable to apply a topical preparation of compounds of this invention to the affected area two to four times a day. Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the APIs may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The API may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Accordingly, in yet another embodiment, the present invention provides the use of a medicament for the treatment of inflammatory conditions, including RA, psoriasis, psoriatic arthritis, pain, COPD, Crohn's disease, and other indications described herein.

In yet another embodiment, there is provided a method of manufacturing a medicament for the treatment of inflammation, the method comprising combining an amount of a compound according to Formulas I, I-B or I-C or I-D with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of TNF-α, IL-1, IL-6, and IL-8 mediated diseases, cancer, and/or hyperglycemia.

If formulated as a fixed dose, such combination products employ the compounds of this invention within the accepted dosage ranges. Compounds of Formulas I, I-B or I-C or I-D may also be administered sequentially with known anti-inflammatory agents when a combination formulation is inappropriate. The invention is not limited in the sequence of administration; compounds of the invention may be administered either prior to, simultaneous with or after administration of the known anti-inflammatory agent.

The compounds of the invention may also be used in co-therapies with anti-neoplastic agents such as other kinase inhibitors, including CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:
1. A compound of Formula I:

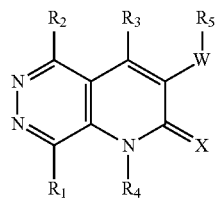

I or a pharmaceutically acceptable salt thereof, wherein
$R^1$ is $C_{1-8}$-alkyl, —$OC_{1-8}$-alkyl, —$SC_{1-8}$-alkyl, —$NHC_{1-8}$-alkyl, —$N(C_{1-8}$-alkyl$)_2$, $C_{2-8}$-alkenyl, $C_{2-8}$-alkynyl or $C_{3-8}$-cycloalkyl, each of which is optionally substituted with 1-5 substituents of $R^6$,
or $R^1$ is a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with 1-5 substituents of $R^6$;
each of $R^2$ and $R^3$, independently, is H, halo, haloalkyl, $NO_2$, CN, $C_{1-6}$-alkyl, $C_{1-6}$-alkoxyl, $C_{1-6}$-thioalkyl, $C_{1-6}$-aminoalkyl, $C_{2-6}$-alkenyl, $C_{2-6}$-alkynyl or $C_{3-6}$-cycloalkyl, each of the $C_{1-6}$-alkyl, $C_{2-6}$-alkenyl, $C_{2-6}$-alkynyl and $C_{3-10}$-cycloalkyl optionally substituted with 1-5 substituents of $R^6$;
$R^4$ is CN, $C(O)R^6$, $C_{1-6}$-alkyl, —$OC_{1-6}$-alkyl, $C_{2-6}$-alkenyl, $C_{2-6}$-alkynyl or $C_{3-6}$-cycloalkyl, each of the $C_{1-6}$-alkyl, —$OC_{1-6}$-alkyl, $C_{2-6}$-alkenyl, $C_{2-10}$-alkynyl and $C_{3-6}$-cycloalkyl optionally substituted with 1-5 substituents of $R^6$;
$R^5$ is a partially or fully saturated or fully unsaturated 3-6 membered monocyclic, ring of carbon atoms optionally including 1-3 heteroatoms selected from O, N, or S, and optionally substituted independently with 1-5 substituents of $R^6$;
each $R^6$, independently, is F, Cl, Br, I, $CF_3$, $C_2F_5$, CN, OH, $NO_2$, $NH_2$, acetyl, oxo, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, —$SO_2C_{1-6}$-alkyl or a saturated or partially or fully unsaturated 5-6 membered monocyclic ring formed of carbon atoms optionally including 1-3 heteroatoms selected from O, N, or S and optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine or diisopropylamine;
W is O, S, NH or $NCH_3$; and
X is O or S.

2. The compound of claim 1, or a pharmaceutically acceptable salt thereof, wherein $R^5$ is a phenyl or pyridyl ring optionally substituted with 1-3 substituents of $R^6$.

3. The compound of claim 1, or a pharmaceutically acceptable salt thereof, wherein $R^1$ is $C_{1-8}$-alkyl, —$OC_{1-8}$-alkyl, —$SC_{1-8}$-alkyl, —$NHC_{1-8}$-alkyl, —$N(C_{1-8}$-alkyl$)_2$, $C_{2-8}$-alkenyl, $C_{2-8}$-alkynyl or $C_{3-8}$-cycloalkyl, each of which is optionally substituted with 1-5 substituents of $R^6$.

4. The compound of claim 1, or a pharmaceutically acceptable salt thereof, wherein $R^1$ is phenyl, pyridyl, pyrimidyl, triazinyl, pyridazinyl, pyrazinyl, thiophenyl, furyl, tetrahydrofuryl, pyrrolyl, tetrahydropyrrolyl, pyrazolyl, imidazolyl, triazolyl, tetrazolyl, thiazolyl, oxazolyl, oxazolinyl, isoxazolyl, isoxazolinyl, oxadiazolyl, isothiazolyl, morpholinyl, piperidinyl, piperazinyl, pyranyl, cyclopropyl, cyclobutyl, cyclopentyl or cyclorhexyl, each of which is optionally substituted with 1-5 substituents of $R^6$.

5. The compound of claim 1, or a pharmaceutically acceptable salt thereof, wherein each of $R^2$ and $R^3$, independently, is H.

6. The compound of claim 1, or a pharmaceutically acceptable salt thereof, wherein $R^4$ is CN, $C(O)R^6$, —$OC_{1-6}$-alkyl, $C_{1-4}$-alkyl$C(O)R^6$, methyl, ethyl, propyl, isopropyl, cyclopropyl, butyl, isobutyl, tert-butyl, pentyl, neopentyl or $C_{1-4}$-alkyl-amino-$C_{1-4}$-alkyl or $C_{1-4}$-dialkylamino$C_{1-4}$-alkyl-.

7. The compound of claim 1, or a pharmaceutically acceptable salt thereof, wherein
$R^1$ is phenyl, pyridyl, pyrimidyl, triazinyl, pyridazinyl, pyrazinyl, thiophenyl, furyl, tetrahydrofuryl, pyrrolyl, tetrahydropyrrolyl, pyrazolyl, imidazolyl, triazolyl, tetrazolyl, thiazolyl, oxazolyl, oxazolinyl, isoxazolyl, isoxazolinyl, oxadiazolyl, isothiazolyl, morpholinyl, piperidinyl, piperazinyl, pyranyl, cyclopropyl, cyclobutyl, cyclopentyl or cyclorhexyl, each of which is optionally substituted with 1-5 substituents of $R^6$;
each of $R^2$ and $R^3$, independently, is H, halo, haloalkyl or $C_{1-4}$-alkyl;
$R^4$ is CN, $C(O)R^6$, —$OC_{1-6}$-alkyl, $C_{1-4}$-alkyl$C(O)R^6$, methyl, ethyl, propyl, isopropyl, cyclopropyl, butyl, isobutyl, tert-butyl, pentyl, neopentyl or $C_{1-4}$-alkyl-amino-$C_{1-4}$-alkyl or $C_{1-10}$-dialkylamino$C_{1-4}$-alkyl-;
$R^5$ is a ring selected from phenyl, pyridyl, pyrimidyl, triazinyl, pyridazinyl, pyrazinyl, thiophenyl, furyl, pyrrolyl, pyrazolyl, imidazolyl, triazolyl, thiazolyl, oxazolyl, isoxazolyl, isothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, cyclopropyl, cyclobutyl, cyclopentyl, cyclohexyl and cycloheptyl, wherein said ring is optionally substituted independently with 1-3 substituents of $R^6$;
each $R^6$, independently, is H, F, Cl, Br, I, $CF_3$, $C_2F_5$, CN, OH, $NO_2$, $NH_2$, acetyl, oxo, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl or —$SO_2C_{1-6}$-alkyl;
W is O, S or NH; and
X is O.

8. The compound of claim 1, or a pharmaceutically acceptable salt thereof, wherein
   $R^1$ is $C_{1-6}$-alkyl, —$OC_{1-6}$-alkyl, —$SC_{1-6}$-alkyl, —$NHC_{1-6}$-alkyl or a ring selected from phenyl, pyridyl, pyrimidyl, pyridazinyl, pyrazinyl, thiophenyl, furyl, tetrahydrofuryl, pyrrolyl, tetrahydropyrrolyl, pyrazolyl, imidazolyl, triazolyl, thiazolyl, oxazolyl, isoxazolyl, isothiazolyl, morpholinyl, piperidinyl, piperazinyl, cyclopropyl, cyclobutyl, cyclopentyl or cyclorhexyl, each of $C_{1-6}$-alkyl, —$OC_{1-6}$-alkyl, —$SC_{1-6}$-alkyl, —$NHC_{1-6}$-alkyl and ring optionally substituted with 1-5 substituents of $R^6$;
   each of $R^2$ and $R^3$, independently, is H, F, Cl, $CF_3$, methyl or ethyl;
   $R^4$ is CN, $C(O)R^6$, —$OC_{1-6}$-alkyl, $C_{1-4}$-alkyl$C(O)R^6$, methyl, ethyl, propyl, isopropyl, cyclopropyl, butyl, isobutyl, tert-butyl, pentyl, $C_{1-4}$-alkyl-amino-$C_{1-4}$-alkyl or $C_{1-4}$-dialkylamino$C_{1-4}$-alkyl-;
   $R^5$ is a ring selected from phenyl, pyridyl, pyrimidyl, triazinyl, pyridazinyl, pyrazinyl, thiophenyl, furyl, pyrrolyl, pyrazolyl, imidazolyl, triazolyl, thiazolyl, oxazolyl, isoxazolyl, isothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, cyclopropyl, cyclobutyl, cyclopentyl, cyclohexyl and cycloheptyl, wherein said ring is optionally substituted independently with 1-3 substituents of $R^6$;
   each $R^6$, independently, is H, F, Cl, Br, I, $CF_3$, $C_2F_5$, CN, OH, $NO_2$, $NH_2$, acetyl, oxo, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl or $C_{1-6}$-thioalkoxyl;
   W is O, S or NH; and
   X is O.

9. The compound of claim 1, or a pharmaceutically acceptable salt thereof, selected from:
   8-(2,4-difluorophenyl)-3-(2,4-difluorophenylamino)-1-methylpyrido[3,2-d]pyridazin-2(1H)-one;
   8-(2,4-difluorophenyl)-3-(4-fluorophenoxy)-1-methylpyrido[3,2-d]pyridazin-2(1H)-one; and
   3-(2,4-difluorophenylamino)-8-(2-fluoro-4-(trifluoromethyl)phenyl)-1-methylpyrido[3,2-d]pyridazin-2(1H)-one;
   8-(2,4-difluorophenyl)-3-((2,4-difluorophenyl)amino)-1-ethylpyrido[2,3-d]pyridazin-2(1H)-one;
   8-(2-chlorophenyl)-3-(2,4-difluorophenoxy)-1-methylpyrido[2,3-d]pyridazin-2(1H)-one;
   3-((2,4-difluorophenyl)amino)-1-methyl-8-(2-methyl-4-(methylsulfonyl)phenyl)pyrido[2,3-d]pyridazin-2(1H)-one;
   3-(2,4-difluorophenoxy)-1-methyl-8-(2-methyl-4-(methylsulfonyl)phenyl)pyrido[2,3-d]pyridazin-2(1H)-one;
   8-(2-chloro-4-(methylsulfonyl)phenyl)-3-((2,4-difluorophenyl)amino)-1-methylpyrido[2,3-d]pyridazin-2(1H)-one;
   8-(2,4-difluorophenyl)-3-((4-fluorophenyl)amino)-1-methylpyrido[2,3-d]pyridazin-2(1H)-one; and
   3-(2,4-difluorophenoxy)-8-(2,4-difluorophenyl)-1-methylpyrido[2,3-d]pyridazin-2(1H)-one.

10. A pharmaceutical composition comprising a compound according to claim 1 and a pharmaceutically acceptable excipient.

11. A pharmaceutical composition comprising a compound according to claim 9 and a pharmaceutically acceptable excipient.

12. A method of preparing a compound according to claim 1, the method comprising the step of reacting a compound 7

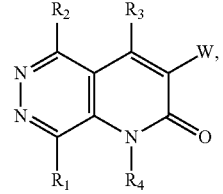

wherein $R^1$, $R^2$, $R^3$, $R^4$ and W are as defined in claim 1, with a boronic acid having a general formula

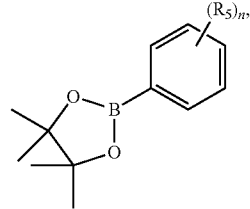

wherein $R^5$ is as defined in claim 1 and n is 0, 1, 2, 3 or 4, to make the compound of claim 1.

* * * * *